(12) United States Patent
Rix et al.

(10) Patent No.: US 7,081,543 B2
(45) Date of Patent: Jul. 25, 2006

(54) BRIDGED BISCYCLOPENTADIENYL LIGANDS AND METHOD OF PREPARATION

(75) Inventors: Francis C. Rix, League City, TX (US); Terry J. Burkhardt, Kingwood, TX (US); Robert T. Li, Houston, TX (US); William T. Haygood, Jr., Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 4 days.

(21) Appl. No.: 11/181,004

(22) Filed: Jul. 13, 2005

(65) Prior Publication Data

US 2005/0250956 A1 Nov. 10, 2005

Related U.S. Application Data

(60) Division of application No. 10/203,017, filed on Oct. 16, 2002, now Pat. No. 6,960,676, which is a continuation of application No. 09/535,357, filed on Mar. 24, 2000, now Pat. No. 6,384,142.

(60) Provisional application No. 60/181,016, filed on Feb. 8, 2000.

(51) Int. Cl.
*C07F 7/22* (2006.01)
*C07F 7/06* (2006.01)
*C07F 7/08* (2006.01)

(52) U.S. Cl. .................... 556/87; 556/95; 556/465; 556/478; 556/489; 556/11; 556/53

(58) Field of Classification Search ............ 556/87, 556/95, 465, 478, 489, 11, 53
See application file for complete search history.

(56) References Cited

U.S. PATENT DOCUMENTS

| | | | |
|---|---|---|---|
| 4,801,730 A | 1/1989 | Stühler et al. ............. 558/313 |
| 5,017,714 A | 5/1991 | Welborn, Jr. ................ 556/12 |
| 5,118,757 A | 6/1992 | McCullough, Jr. ........... 525/53 |
| 5,145,819 A | 9/1992 | Winter et al. .............. 502/117 |
| 5,166,268 A | 11/1992 | Ficker ....................... 525/198 |
| 5,191,042 A | 3/1993 | Cozewith ................... 526/281 |
| 5,194,619 A | 3/1993 | Reuschling et al. ........ 546/348 |
| 5,250,631 A | 10/1993 | McCullough, Jr. .......... 525/322 |
| 5,258,464 A | 11/1993 | McCullough, Jr. et al. . 525/244 |
| 5,304,614 A | 4/1994 | Winter et al. .............. 526/127 |
| 5,314,973 A | 5/1994 | Welborn, Jr. ............... 526/126 |
| 5,347,026 A * | 9/1994 | Patsidis et al. ............. 556/87 |
| 5,362,782 A | 11/1994 | McCullough, Jr. et al. . 524/108 |
| 5,374,752 A | 12/1994 | Winter et al. ............... 556/11 |
| 5,382,631 A | 1/1995 | Stehling et al. ............ 525/240 |
| 5,401,817 A * | 3/1995 | Palackal et al. ............ 526/127 |
| 5,486,585 A | 1/1996 | Murata et al. .............. 526/130 |
| 5,541,350 A | 7/1996 | Murata et al. .............. 556/10 |
| 5,543,373 A | 8/1996 | Winter et al. .............. 502/103 |
| 5,612,428 A | 3/1997 | Winter et al. .............. 526/127 |
| 5,623,022 A | 4/1997 | Sugano et al. ............. 525/247 |
| 5,631,335 A * | 5/1997 | Alt et al. ................... 526/126 |
| 5,672,668 A | 9/1997 | Winter et al. .............. 526/127 |
| 5,693,836 A | 12/1997 | Winter et al. .............. 556/11 |
| 5,708,101 A | 1/1998 | Bercaw et al. ............. 526/127 |
| 5,712,344 A | 1/1998 | McCullough, Jr. et al. ... 525/88 |
| 5,747,576 A | 5/1998 | Sobajima et al. .......... 524/451 |
| 5,770,753 A | 6/1998 | Kuber et al. ............... 556/11 |
| 5,830,821 A | 11/1998 | Rohrmann et al. ......... 502/117 |
| 5,840,644 A | 11/1998 | Kuber et al. ............... 502/117 |
| 5,840,808 A | 11/1998 | Sugimura et al. .......... 525/268 |
| 5,854,354 A | 12/1998 | Ueda et al. ................ 525/322 |
| 5,942,587 A | 8/1999 | Arjunan et al. ............ 526/281 |
| 5,948,839 A | 9/1999 | Chatterjee ................. 524/108 |
| 5,990,220 A | 11/1999 | Sobajima et al. .......... 525/449 |
| 5,990,242 A | 11/1999 | Naga et al. ................ 525/95 |
| 6,004,897 A | 12/1999 | Imuta et al. ............... 502/103 |
| 6,087,518 A | 7/2000 | Gately ....................... 556/410 |
| 6,180,810 B1 | 1/2001 | Gately ....................... 556/410 |
| 6,342,566 B1 | 1/2002 | Burkhardt .................. 525/191 |
| 6,384,142 B1 | 5/2002 | Burkhardt .................. 525/191 |
| 6,472,474 B1 | 10/2002 | Burkhardt .................. 525/191 |
| 6,492,465 B1 | 12/2002 | Burkhardt .................. 525/247 |

FOREIGN PATENT DOCUMENTS

| | | |
|---|---|---|
| DE | 3244752 A1 | 6/1984 |
| DE | 41 30 429 | 3/1993 |
| EP | 399348 A2 | 11/1990 |
| EP | 376154 | 1/1991 |
| EP | 485823 A1 | 9/1992 |
| EP | 571882 A2 | 12/1993 |
| EP | 0 629 632 A | 12/1994 |
| EP | 628565 A1 | 12/1994 |
| EP | 641807 A2 | 3/1995 |
| EP | 0 657 500 | 6/1995 |
| EP | 284708 B1 | 1/1996 |
| EP | 485822 B1 | 7/1996 |
| EP | 776913 A2 | 6/1997 |
| EP | 0 576 970 | 3/1998 |
| EP | 0 870 804 A1 | 10/1998 |
| EP | 0 890 590 A1 | 1/1999 |

(Continued)

OTHER PUBLICATIONS

Alt, Helmut G., et al., *ansa*-Metallocenkomplexe des Typs ($C_{13}H_8$-$SiR_2$-$C_9H_6$-$_1R'_n$)$ZrCl_2$ (n=0,1; R=Me, Ph, Alkenyl; R'=Alkyl, Alkenyl): Selbstimmobilisierende Katalysatorvorstufen für die Ethylenpolymerisation, Journal of Organometallic Chemistry, 562, (1998), pp. 229-253.

(Continued)

*Primary Examiner*—Porfirio Nazario-Gonzalez

(57) ABSTRACT

The present invention relates to ligands and the synthesis of those ligands for use in metallocene complexes. More particularly, the present invention relates to the synthesis of diarylsilyl bridged biscyclopentadienes using diarylsilyldisulfonates. Even more particularly, the present invention describes Group IV metallocenes containing diarylsilyl bridged bis-cyclopentadienyl ligands prepared from contacting a diarylsilyldisulfonate with an organometallic indenyl reagent.

7 Claims, No Drawings

FOREIGN PATENT DOCUMENTS

| EP | 0 962 474 A | 12/1999 |
|----|-------------|---------|
| EP | 985674 A1 | 3/2000 |
| JP | 10101689 | 4/1998 |
| WO | WO 98/40331 | 9/1998 |
| WO | WO 99/12943 | 3/1999 |
| WO | 99/38871 | 8/1999 |

OTHER PUBLICATIONS

Bhattacharya, S. N., et al., *Reactions of Tetraorganotin Derivatives with Chlorosulphonic Acid*, Indian J. Chem., vol. 16A, (Dec. 1978), pp. 1108-1110.

Castany, M. H., et al., *Synthese De Germyl Perfluoroalcanes Sulfonates Quelques Aspects De Leur Reactivite En Tant Qu 'Agent De Germylation*, Synth. React. Inorg. Met.-Org. Chem, 28(5), (1998), pp. 781-801. (contains Abstract).

Harrison, Philip G., et al., *Structural Studies in Main Group Chemistry XV*.Di- and Tri-Organotin Arylsulphonates*, Journal of Organometallic Chemistry, 114 (1976), pp. 47-52.

Ihara, Eiji, et al., *Synthesis and Olefin Polymerization Catalysis of New Divalent Samarium Complexes with Bridging Bis(cyclopentadienyl) Ligands*, Organometallicss, 17, (1998), pp. 3945-3956.

Kaminsky, W. et al, *Standardized polymerizations of ethylene and propene with bridged and unbridged metallocene derivatives: a comparison*, Makromol. Chem. vol. 193, pp. 1643-1651, Huthig & Wepf Verlag, Basel (1992).

Kolosova, N.D., et al., *Synthesis of tricyclopentadienyl-, alkyl-, and phenylcyclopentadienyltin chlorides*, Dokl. Akad. Nauk SSSR, 218(1), (1974), pp. 117-119. (Abstract).

McMaster, A. D., et al., *Stereochemically Nonrigid Silanes, Germanes, and Stannanes. 10. Diastereoisomerism and Metallotropic Behavior in Polyindenyl Derivatives of Germanium and Tin. Facile Stereomutation*, J. Am. Chem. Soc., v. 104, No. 8 (1982), pp. 2109-2112.

Patsidis, Konstantinos, et al., *The synthesis, characterization and polymerization behavior of ansa cyclopentadienyl fluorenyl complexes; the X-ray structures of the complexes [(C$_{13}$H$_8$) SiR$_2$(C$_3$H$_4$)]ZrCl$_2$ (R=Me or Ph)*, Journal of Organometallic Chemistry 509 (1996) pp. 63-71.

Patsidis, K., et al., *Ansa-bis(fluorenyl) complexes as homogeneous catalysts for propylene polymerization*, Iav. Akad. Nauk, Ser. Khim. 9 (1996) pp. 2334-2339. (Abstract).

Schmeisser, Martin, et al., *Zur Chemie der Perfluoralkansulfonsäuren*, Chem. Ber., 103 (1970) pp. 868-879. (contains Abstract).

Soga, Kazuo, et al., *Synthesis of a dinuclear ansa-zirconocene catalyst having a biphenyl bridge and application to ethene polymerization*, Journal of Molecular Catalysis A: Chemical, 128 (1998), pp. 273-278.

Spaleck, Walter, et al., *Stereospecific Metallocene Catalysts: Scope and Limits of Rational Catalyst Design*, 1297b Macromolecular Symposia 89 (1995) pp. 237-247.

Uhlig, W., *Alkinylsubstituierte Silyltriflate—Synthese und Reaktivität*, Z. anorg. Allg. Chem. 603 (1991) pp. 109-117. (contains Abstract).

Uhlig, W., et al., *Zur Synthese neuartiger Triflate der 14. Gruppe*, Journal of Organometallic Chemistry 409 (1991) pp. 377-383. (contains Abstract).

J. C. Randall, "Sequence Distributions versus Catalyst Site Behavior of in Situ Blends of Polypropylene and Poly (ethylene-co-propylene)", Journal of Polymer Science: Part A: Polymer Chemistry, vol. 36, 1527-1542, (1998) John Wiley & Sons, Inc.

Westphal, et al.; "Further Studies On Matellocene ULDPE/ PP Blends Impact—Morphology Relationships", Annu. Tech. Con.—Soc. Plast. Eng., 55th (vol. 2), 2631-2635, (1997).

* cited by examiner

BRIDGED BISCYCLOPENTADIENYL LIGANDS AND METHOD OF PREPARATION

CROSS REFERENCE TO RELATED APPLICATION

The present application is a divisional of U.S. application Ser. No. 10/203,017, filed Oct. 16, 2002, now U.S. Pat. No. 6,960,676 which is a continuation of U.S. Ser. No. 09/535,357 filed Mar. 24, 2000, issued as U.S. Pat. No. 6,384,142; and to Provisional U.S. Ser. No. 60/181,016, filed Feb. 8, 2000.

FIELD

The present invention relates to ligands and the synthesis of those ligands for use in metallocene complexes. More particularly, the present invention relates to the synthesis of diarylsilyl bridged biscyclopentadienes using diarylsilyldisulfonates. Even more particularly, the present invention describes Group 4 metallocenes containing diarylsilyl bridged bis-cyclopentadienyl ligands prepared from contacting a diarylsilyldisulfonate with an organometallic indenyl reagent.

BACKGROUND

Metallocene complexes of Group 4 from the Periodic Table have been widely used as precursors of catalysts for olefin polymerization. The substitution of the cyclopentadienyl ligands used in these metallocenes is widely recognized to play a critical role in determining the catalyst system's polymerization activity and selectivity. It is also well known that if two cyclopentadienyl ligands are bridged by a common substituent such as a dihydrocarbyl silyl group. The catalysts properties can change dramatically relative to the non-silyl bridged analogue.

For example, the unbridged (2-methylindenyl)$ZrCl_2$/MAO (MAO=methylalumoxane) is a poor catalyst system for isotactic polypropylene production, while in contrast, rac-$Me_2Si$(2-methylindenyl)$_2ZrCl_2$/MAO polymerizes propylene to a highly isotactic polymer. Also, an increase in molecular weight can be observed by a simple change in bridging group. For instance, a 23% increase in molecular weight for ethylene polymerization was observed upon changing the bridging group from $Me_2Si$ in $Me_2Si$(indenyl)$_2$ $ZrCl_2$/MAO to $Ph_2Si$ in $Ph_2Si$(indenyl)$_2ZrCl_2$/MAO in 193 Makromol. Chem. 1643 (1992), and EP 0399348A2.

The $Ph_2Si$(indene)$_2$ ligand was prepared from $Ph_2SiCl_2$ and two equivalents of indenyl lithium in only 42% yield, as disclosed in EP 0376154, herein incorporated by reference for purposes of U.S. patent practice. The preparation of the metallocene $Ph_2Si$(2-methylindenyl)$_2$ $ZrCl_2$ from $ZrCl_4$ and $Ph_2Si$(2-methylindenyl lithium)$_2$ has been reported but was without the procedure for preparing Ph2Si(2-methylindene)$_2$, as in EP 485822A1, EP 485823A1, herein incorporated by reference for purposes of U.S. patent practice.

Silyl bridged metallocenes are typically prepared from reaction of organometallic cyclopentadienyl ligands and dihydrocarbylsilyldichlorides. There has also been an example of using dimethysilylditriflate as the silylating agent disclosed in WO 99/38871. However, the use of diarylsilylditriflates has not received similar scrutiny. These reagents are readily prepared from diarlysilyldichlorides and silver triflates or protonolysis of tetraarylsilanes with triflic acid discussed in 103 Chem. Ber. 868 (1970); 409 J. Organomet. Chem. 377 (1991). This invention encompasses the process of using diarylsilyldisulfonates to prepare diarylsilylbridged dicyclopentadienyl ligands and metallocenes containing diarylsilylbridged dicyclopentadienyl ligands and polymers prepared with metallocenes containing diarylsilylbridged dicyclopentadienyl ligands.

SUMMARY

The present invention encompases a method of forming a compound capable of bonding with a Group 4 transition metal to form a metallocene catalyst component suitable for olefin polymerization processes, the method comprising combining in a suitable solvent a diarylmetaldisulfonate moiety with a organometallic cyclopentadienyl moiety to form a diarylmetal bridged biscyclopentadienyl compound.

The diarylmetaldisulfonate is described as follows:

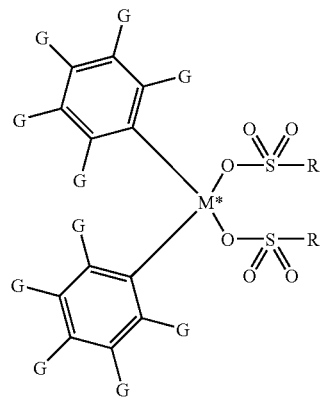

wherein G is the same or different and are hydrogen, alkyl, haloalkyl, vinyl, aryl, alkynyl, silyl, germyl, amine, ammonium, phosphine, phosphonium, ether, thioether, fluoro, chloro, bromo, iodo, borane, borate, alane or aluminate groups or any combination of such groups; and wherein adjacent G groups from each aryl group may join to form a ring system of 2 to 8 carbon atoms and also contain an amine, silyl, or ether group; and wherein the aryl groups may be joined at the corresponding ortho (2) positions by a covalent bond;

and wherein the aryl groups may also be heterocycles that are aromatic;

and wherein the aryl rings may also be substituted by annulated rings such annulated aryl rings are napthylene, tetrahydronapthyl, phenanthryl and fluorenyl;

and wherein the aryl rings may also be substituted by additional silylsulfonates;

and wherein the two aryl groups bound to the silyldisulfonate fragment may also be joined together directly, as in a substituted biphenyl derivative or by linker groups; wherein the linker group is an alkyl, vinyl, phenyl, alkynyl, silyl, germyl, amine, ammonium, phosphine, phosphonium, ether, thioether, borane, borate, alane or aluminate groups;

wherein M* is Si, Sn or Ge; and wherein the R groups may be the same or different, and are an alkyl, perhaloalkyl, phenyl, perhalophenyl.

The organometallic cyclopentadienyl moiety is described as follows:

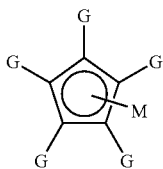

wherein G is the same or different and are a hydrogen, alkyl, haloalkyl, vinyl, aryl, alkynyl, silyl, germyl, amine, ammonium, phosphine, phosphonium, ether, thioether, fluoro, chloro, bromo, iodo, borane, borate, alane or aluminate groups or any combination of such groups; and wherein adjacent G groups from each aryl group may join to form a ring system of 2 to 8 carbon atoms and also contain an amine, silyl, or ether group; and wherein M is a metal such as Li, Na, or K.

The ligand thus described and synthesized can be used to make a Group 4 metallocene suitable for olefin polymerization, in particular homopolymers or copolymers of polypropylene and ethylene, and impact copolymers thereof.

DETAILED DESCRIPTION OF THE INVENTION

Definition of Terms

The term "cyclopentadienyl" is used to refer to cyclopentadienyl, indenyl, fluorenyl, azulenyl, azaindenyl, azapentalenyl, thiopentalenyl groups, and other ring systems capable of binding to a metal center. These cyclopentadienyl, indenyl, fluorenyl and other ring systems may be substituted or unsubstituted. The use of "biscyclopentadienyl" refers to any combination of two of these groups.

The phrase "catalyst system" refers to the metallocene and other activators and cocatalysts used in olefin polymerization, including MAO and borane activators.

The term "hydrocarbyl" refers to any alkyl, alkenyl, alkynyl or aryl group; the two hydrocarbyls of a dihydrocarbyl may be the same or different.

The term "sulfonate" refers to a functional group of the structure —OSO$_2$R, where R may be a hydrocarbyl, halogenated hydrocarbyl, perfluorocarbyl, or CF$_3$.

The term "triflate" refers to a trifluoromethyl sulfonate functional group: —O$_3$SCF$_3$.

For purposes of this invention, all Periodic Table "Groups" recited herein are based upon the notation of the Periodic Table of Elements as described in Hawley's Chemical Dictionary, 11th Ed., Van Nostrand Reinhold, N.Y. (1987).

Synthesis of Ligand

Diarylsilyl bridged cyclopentadienyl ligands are prepared by contacting a diarylsilyldisulfonate with an organometallic indenyl reagent, as shown below in reaction (A):

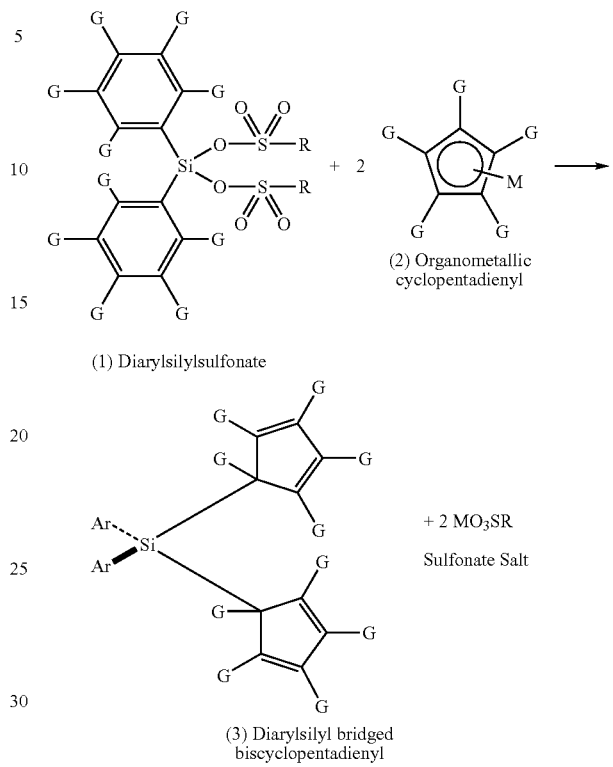

wherein the *diarylsilyldisulfonate* (1) moiety has two components: the aryl groups and sulfonate groups. The aryl groups may be the same or different. The aryl groups may contain any functional group containing any elements that do not react with the diarylsilyldisulfonate, organometallic indenyl reagent or other components of the reaction medium in such a manner as to completely prevent formation of a diarylsilyl bridged bisindenyl compound.

In one embodiment, the aryl groups may contain any functional group containing Group 13–17 elements that do not react with the diarylsilyldisulfonate, organometallic indenyl reagent or other components of the reaction medium in such a manner as to completely prevent formation of a diarylsilyl bridged bisindenyl compound.

G may be the same or different. Non-limiting examples of G include hydrogen, alkyl, haloalkyl, vinyl, aryl, alkynyl, silyl, germyl, amine, ammonium, phosphine, phosphonium, ether, thioether, fluoro, chloro, bromo, iodo, borane, borate, alane and aluminate groups or any combination of such groups that do not completely prohibit formation of diarylsilyl bridged bisindenyl compounds. Adjacent G groups from each aryl group may join to form a ring system of 2 to 8 carbon atoms and also contain an amine, silyl, or ether group. Also, the aryl groups may be joined at the corresponding ortho (2) positions and/or the meta (3) by a covalent bond.

Metals other than Si may be useful for the diarylmetaldisulfonate group (1) above such as Sn or Ge.

The aryl groups may also be heterocycles that are aromatic. Aromatic heterocycles contain 4n+2 pi electrons (where n is a non-zero integer) in the heterocycle ring directly bound to silicon.

The aryl rings may also be substituted by annulated rings. Non-limiting examples of such annulated aryl rings are napthyl, tetrahydronapthyl, phenanthryl and fluorenyl.

The aryl rings may also be substituted by additional silylsulfonates. In this manner, compounds containing greater than two indenyl rings may be prepared allowing the preparation of multimetallic polymerization precatalysts.

The two aryl groups bound to the silyldisulfonate fragment may also be joined together directly, as in a substituted biphenyl derivative or by linker groups. The linker group may be an alkyl, vinyl, phenyl, alkynyl, silyl, germyl, amine, ammonium, phosphine, phosphonium, ether, thioether, borane, borate, alane or aluminate groups. The two aryl groups may be polycyclic hydrocarbons with aromatic rings directly coordinated to silicon.

Diarylmetaldisulfonate (1)

The diarylsilyldisulfonate (1) from reaction (A) above can be described more generally as a diarylmetaldisulfonate, and include as a metal Ge or Sn. More particularly, (1) is described as follows:

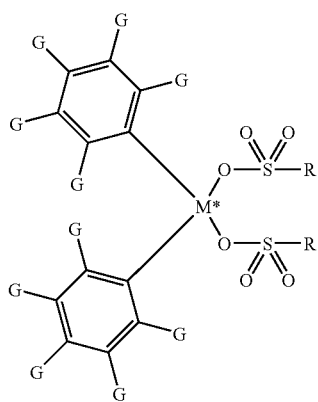

wherein G is the same or different. Non-limiting examples of G include hydrogen, alkyl, haloalkyl, vinyl, aryl, alkynyl, silyl, germyl, amine, ammonium, phosphine, phosphonium, ether, thioether, fluoro, chloro, bromo, iodo, borane, borate, alane and aluminate groups or any combination of such groups that do not completely prohibit formation of diarylsilyl bridged bisindenyl compounds. Adjacent G groups from each aryl group may join to form a ring system of 2 to 8 carbon atoms and also contain an amine, silyl, or ether group. Also, the aryl groups may be joined at the corresponding ortho (2) positions by a covalent bond;

and wherein the aryl groups may also be heterocycles that are aromatic;

the aryl rings may also be substituted by annulated rings such annulated aryl rings are napthyl, tetrahydronapthyl, phenanthryl and fluorenyl;

the aryl rings may also be substituted by additional silylsulfonates. In this manner, compounds containing greater than two indenyl rings may be prepared allowing the preparation of multimetallic polymerization precatalysts; and the two aryl groups bound to the silyldisulfonate fragment may also be joined together directly, as in a substituted biphenyl derivative or by linker groups. The linker group may be an alkyl, vinyl, phenyl, alkynyl, silyl, germyl, amine, ammonium, phosphine, phosphonium, ether, thioether, borane, borate, alane or aluminate groups, wherein the two aryl groups may be a polycyclic hydrocarbon with aromatic rings directly coordinated to silicon;

wherein M* is Si, Sn or Ge.

Also, the R groups may be the same or different, and are an alkyl, perhaloalkyl, phenyl, perhalophenyl. In one embodiment, The R group is a perfluoro substituted group, and in yet another embodiment the R group is a $CF_3$ group.

Non-limiting examples of diarylsilyldisulfonates (1) from reaction (A) are as follows:

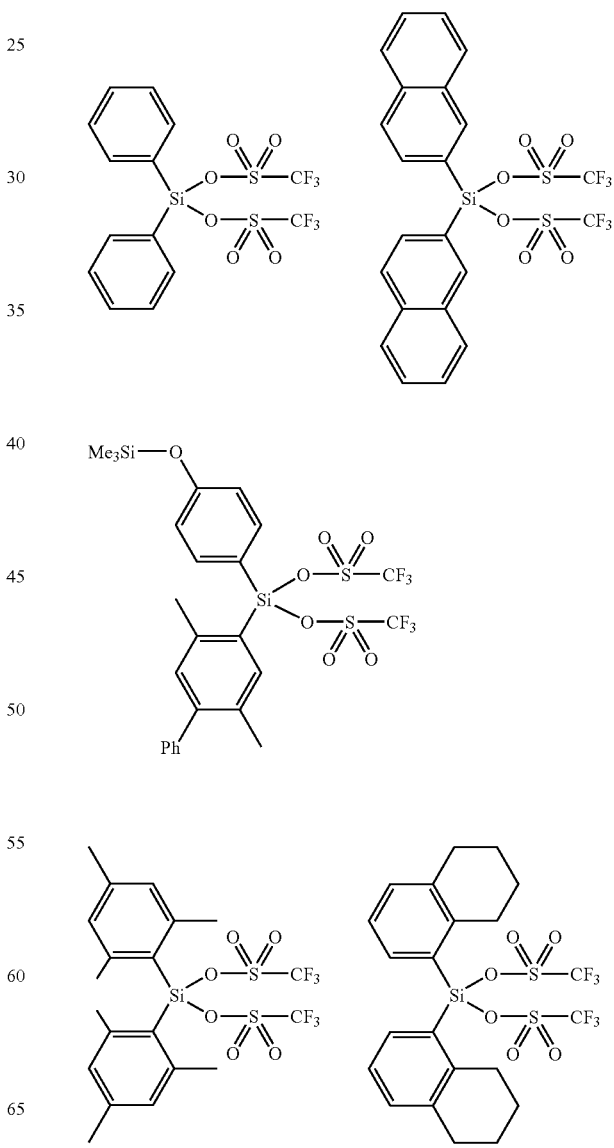

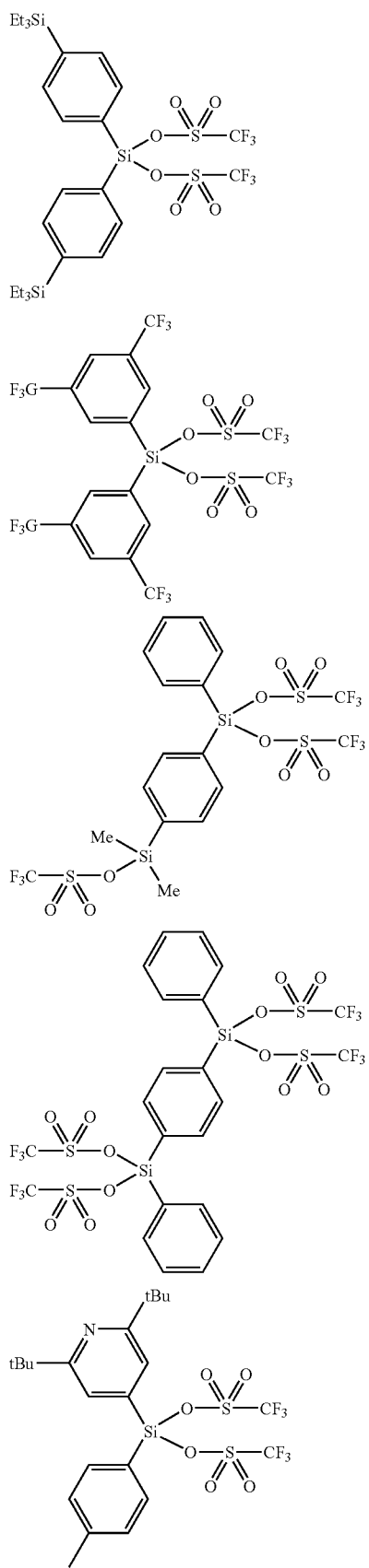

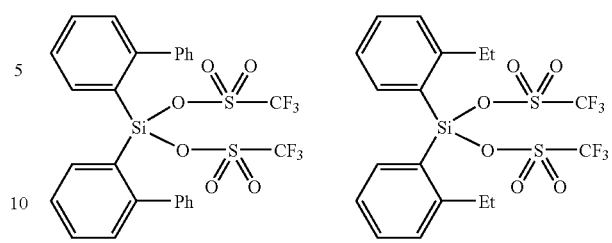

The two aryl groups bound to the silyldisulfonate fragment may also be joined together directly, as in a substituted biphenyl derivative or by linker groups. The linker group may be an alkyl, vinyl, phenyl, alkynyl, silyl, germyl, amine, ammonium, phosphine, phosphonium, ether, thioether, borane, borate, alane, or aluminate groups, wherein the two aryl groups may be a polycyclic hydrocarbon with aromatic rings directly coordinated to silicon. Non-limiting examples of these are as follows:

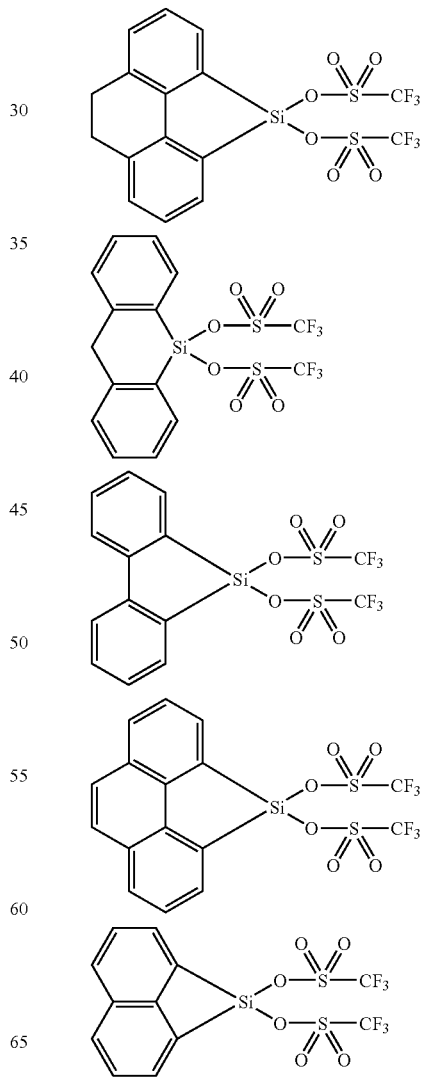

-continued

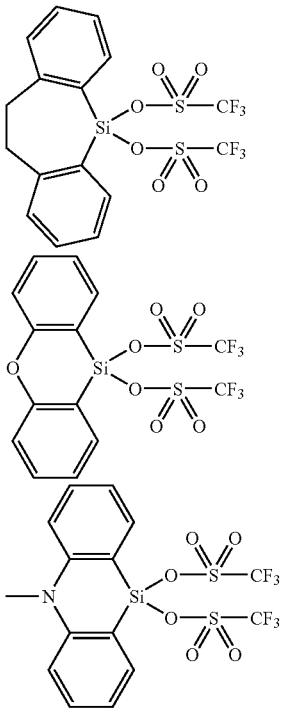

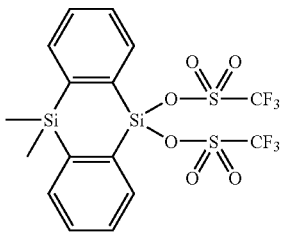

The diarylsilyldisulfonate groups listed above can be stated by their respective nomenclature terms as follows:
diphenylsilylditriflate
di-2-naphthylsilylditriflate
(2-methyl-4-phenyl-5-methyl)(4-trimethylsiloxy)silylditriflate
di(2,4,6-trimethylphenyl)silylditriflate
di-5-tetrahydronaphthylsilylditriflate
di(4-triethylsilylphenyl)silylditriflate
di(3,5-ditrifluoromethylphenyl)silylditriflate
(4-dimethysilyltriflate)(phenyl)silylditriflate
di(diphenylsilylditriflate)
bis(4-methylphenyl)(2,5-di-tert-butylpyridine)silylditriflate
di(biphenyl)silylditriflate
di(2-ethylphenyl)silylditriflate
4,5-(9,10-dihydrophenanthryl)silylditriflate
4,4'-methylene-3,3-'silylditriflate
biphenylsilylditriflate
phenanthra-4,5-silylditriflate
naptha-4,5-silylditriflate
4,4'-ethylene-3,3'-silylditriflate
di-1,1'-oxyphenyl-2,2'-silylditriflate
di-1,1'-methylamine-2,2'-silylditriflate
di-1,1'-dimethylsilyl-2,2'-silylditriflate, and the like.

The Sn or Ge analogs, for example, diphenylstannylditriflate or diphenylgermylditriflate, are also possible for the diphenylmetalditriflate (1).

*Organometallic Cyclopentadienyl Moiety* (2). Referring to reaction (A) above, the organometallic cyclopentadienyl moiety (1) may be more generally described as follows:

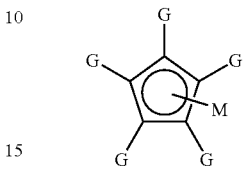

wherein M is a metal such as Li, Na, or K. M may also be Mg, Ca, Hg or other suitable metal. One skilled in the art would know that when M has a formal oxidation state of n, n−1 additional anionic are also coordinated to M. For example, when M is Mg, a second anionic ligand about M is necessary, such as a halide, or a second cyclopentadienyl moiety. The G group is as defined for the diarylsilyldisulfonate (1) moiety.

The cyclopentadienyl ring system may be substituted with any functional group, G, containing any elements, that do not react with the diarylsilyldisulfonate, organometallic cyclopentadienyl reagent or other components of the reaction medium in such a manner as to completely prevent formation of a diarylsilyl bridged biscyclopentadienyl compound. More preferably, aryl groups may contain any functional group containing Group 13–17 elements that do not react with the diarylsilyldisulfonate, organometallic cyclopentadienyl reagent or other components of the reaction medium in such a manner as to completely prevent formation of a diarylsilyl bridged biscyclopentadienyl compound.

The cyclopentadienyl ring system may be substituted with alkyl, perhaloalkyl, vinyl, aryl, alkynyl, silyl, germyl, amine, ammonium, phosphine, phosphonium, ether, thioether, fluoro, chloro, bromo, iodo, borane, borate, alane and aluminate groups or any combination of such groups that do not completely prohibit formation of diarylsilyl bridged biscyclopentadienyl compounds. The cyclopentadienyl ring system may also contain annulated rings.

Embodiments of the organometallic cyclopentadienyl (2) from reaction (A) above are shown below, wherein "tBu" is a tertiary butyl radical:

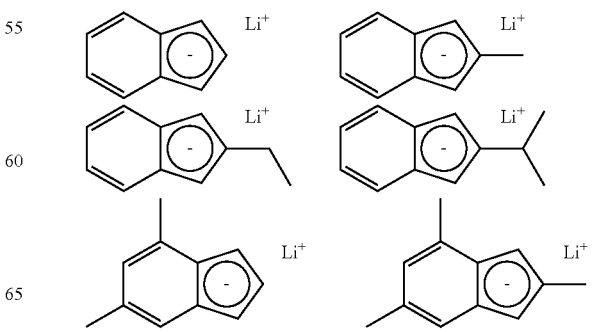

-continued
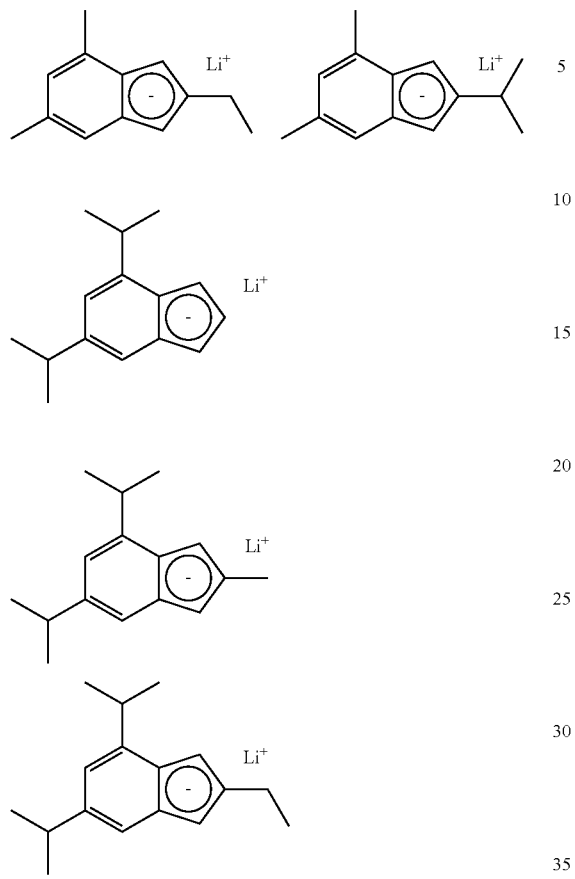
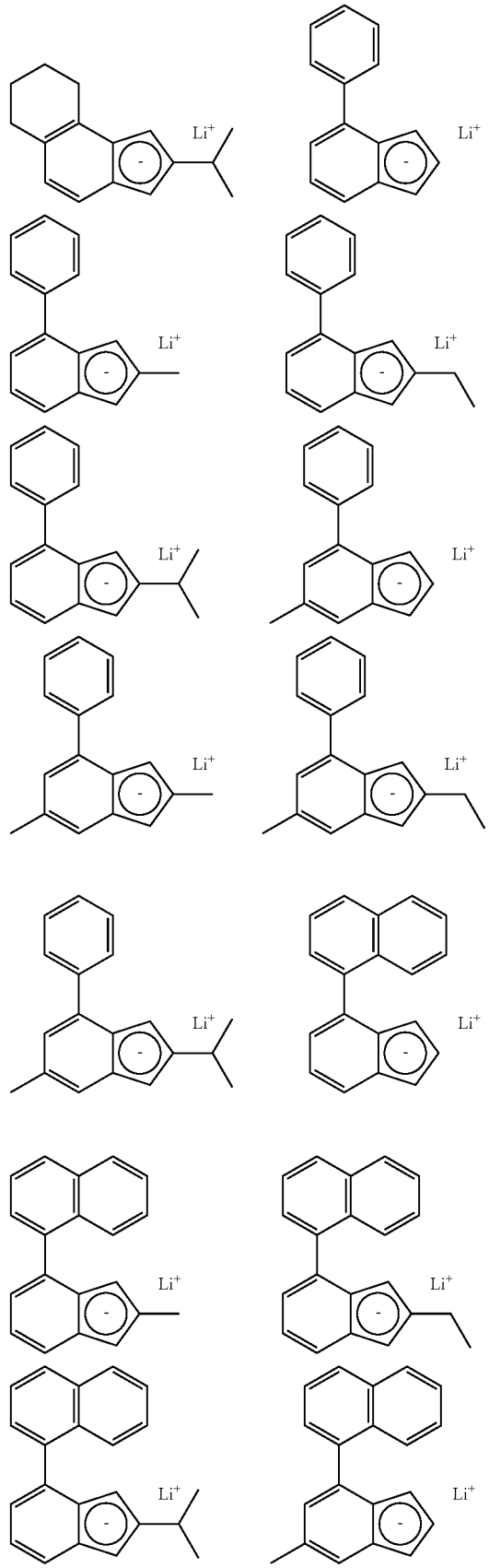

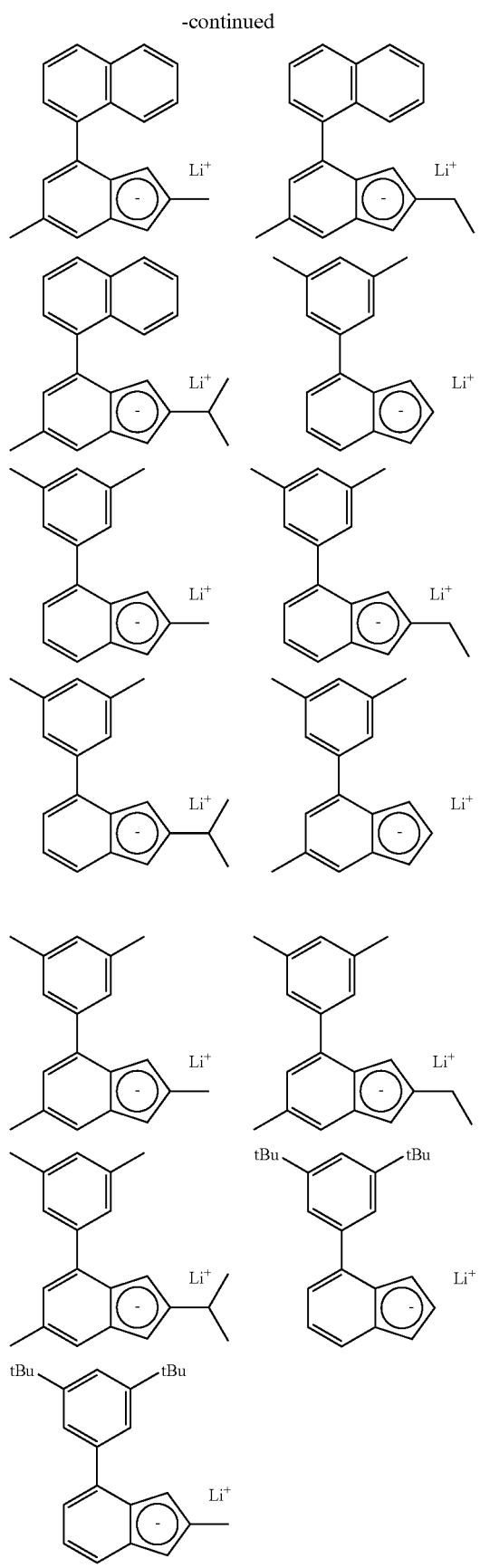
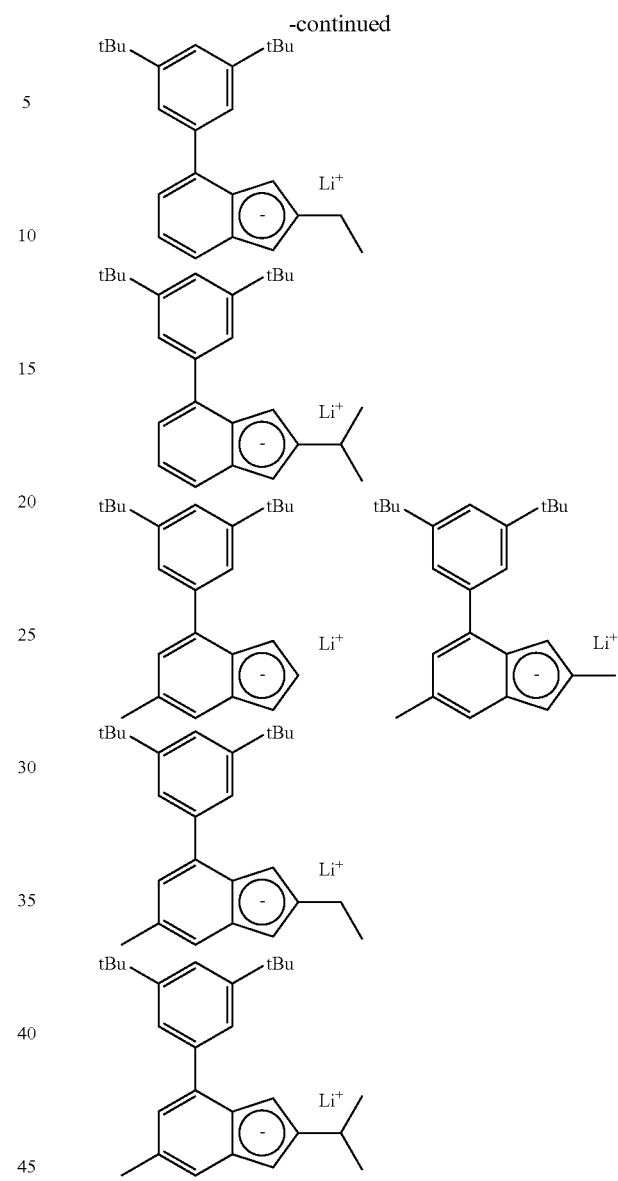

The organometallic cyclopentadienyl groups listed above can be stated by their respective nomenclature terms as follows:

indenyl lithium,
2-methylindenyl lithium,
2-ethylindenyl lithium,
2-isopropylindenyl lithium,
4,6-dimethylindenyl lithium,
2,4,6-trimethylindenyl lithium,
2-ethyl-4,6-dimethylindenyl lithium,
2-isopropyl-4,6-dimethylindenyl lithium,
4,6-diisopropylindenyl lithium,
2-methyl-4,6-diisopropylindenyl lithium,
2-ethyl-4,6-diisopropylindenyl lithium,
4,5-benzoindenyl lithium,
4,5-benzo-2-methylindenyl lithium,
4,5-benzo-2-ethylindenyl lithium,
4,5-benzo-2-isopropylindenyl lithium,
4,5-cyclohexylindenyl lithium,
4,5-cyclohexyl-2-methylindenyl lithium, 4,5-cyclohexyl-2-ethylindenyl lithium, 4,5-cyclohexyl-2-isopropylindenyl lithium, 4-phenylindenyl lithium, 2-methyl-4-phenylindenyl lithium, 2-ethyl-4-phenylindenyl lithium, 2-isopropyl-4-phenylindenyl lithium, 4-phenyl-6-methylindenyl lithium, 2,6-dimethyl-4-phenylindenyl lithium, 2-ethyl-4-phenyl-6-methylindenyl lithium, 2-isopropyl-4-phenyl-6-methylindenyl lithium, 4-[1-naphthyl]indenyl lithium, 2-methyl-4-[1-naphthyl]indenyl lithium, 2-ethyl-4-[1-naphthyl]indenyl lithium, 2-isopropyl-4-[1-naphthyl]indenyl lithium, 4-naphtha-6-methylindenyl lithium, 2,6-dimethyl-4-[1-naphthyl]indenyl lithium, 2-ethyl-4-[1-naphthyl]-6-methylindenyl lithium, 2-isopropyl-4-[1-naphthyl]-6-methylindenyl lithium, 4-(3,5-dimethylphenyl)indenyl lithium, 2-methyl-4-(3,5-dimethylphenyl)indenyl lithium, 2-ethyl-4-(3,5-dimethylphenyl)indenyl lithium, 2-isopropyl-4-(3,5-dimethylphenyl)indenyl lithium, 6-methyl-4-(3,5-dimethylphenyl)indenyl lithium, 2,6-dimethyl-4-(3,5-dimethylphenyl)indenyl lithium, 2-ethyl-4-(3,5-dimethylphenyl)-4-methylindenyl lithium, 2-isopropyl-4-(3,5-dimethylphenyl)6-methylindenyl lithium, 4-(3,5-di-tert-butylphenyl)indenyl lithium, 2-methyl-4-(3,5-di-tert-butylphenyl)indenyl lithium, 2-ethyl-4-(3,5-di-tert-butylphenyl)indenyl lithium, 2-isopropyl-4-(3,5-di-tert-butylphenyl)indenyl lithium, 6-methyl-4-(3,5-di-tert-butylphenyl)indenyl lithium, 2,6-dimethyl-4-(3,5-di-tert-butylphenyl)indenyl lithium, 2-ethyl-4-(3,5-di-tert-butylphenyl)-6-methylindenyl lithium, 2-isopropyl-4-(3,5-di-tert-butylphenyl)6-methylindenyl lithium, and the like.

Synthesis of Diarylsilyl Bridged Bis-cyclopentadienyl Compounds. The reaction of diarylsilyldisulfonate and the organometallic cyclopentadienyl reagent (two equivalents of reactive cyclopentadienyl group per diarylsilyldisulfonate) yields a diarylsilyl bridged biscyclopentadienyl compound and equivalents of sulfonate salt as shown in reaction (A) above. The aryl groups (Ar) shown in the structure labeled (3) in reaction (A) above corresponds to the G substituted aryl groups of the corresponding diarylsilyldisulfonate (1).

In general, the diarylsilyl bridged biscyclopentadienyl compound (3) has the following structure:

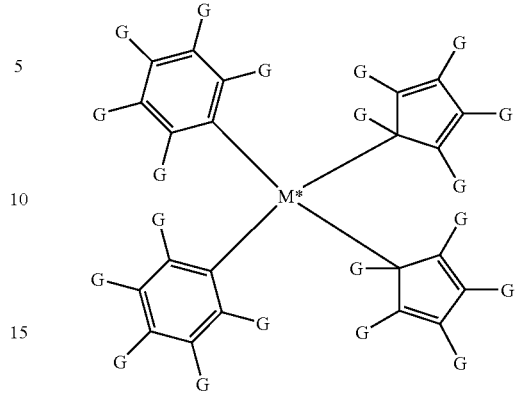

wherein the G groups and M* are as defined above.

The reaction in (A) can proceed in solvents tolerant of the functional groups present. Typical solvents include diethyl ether and toluene or benzene. Once formed, the diarylsilyl bridged biscyclopentadienyl compound and sulfonate salts may be used directly in subsequent syntheses or the sulfonate salt may be removed at this stage. Removal of the salt may be achieved by filtration of the reaction products in a hydrocarbon solvent or extraction with water. If the sulfonate is lithium triflate and the diarylsilyl bridged biscyclopentadienyl compound is poorly soluble in ether, the soluble lithium triflate may be fairly removed by filtration and ether washing. The diarylsilyl bridged biscyclopentadienyl compound can then be isolated and purified, if necessary, by standard methods.

Desirable embodiments of the diarylsilyl bridged biscyclopentadienyl compounds include diphenylsiladiyl(2-methylindenyl); diphenylsiladiyl(2-methyl-4-phenylindenyl); and diphenylsiladiyl(2-methyl-4-[1-naphthyl]indenyl).

This method of synthesis offers an improvement in yield from 42% over the previously reported preparation of $Ph_2Si$ (indene) from $Ph_2SiCl_2$ with two equivalents of cyclopentadienyl lithium. The diphenylsilyldisulfonate route can also be used for preparing diphenylsilyl bridged 2-alkylindene complexes from indenes such as 2-methylindene, 2-methyl-4-phenylindene and 2-methyl-4-[1-napthyl]indene. Comparative examples indicate that the $Ph_2SiCl_2$ method is ineffective for bridging 2-alkylindenyl lithiums such as 2-methylindenyl lithium and 2-methyl-4-phenylindenyl lithium.

Metallocene Synthesis

Diarylsilyl bridged biscyclopentadienyl compounds may be converted to metallocenes by any appropriate method. Some standard methods include direct reaction of the neutral diarylsilyl bridged bicyclopentadiens with $M(NR_2)_4$ (M=Ti, Zr, Hf) as reported by Jordan in 15 *Organometallics* 4045 (1996)). Double deprotonation of the diarylsilyl bridged bicyclopentadiens with reagents such as alkyl lithiums afford diarylsilyl bridged cyclopentadienyl dilithium reagents which may be reacted with $MX_2Y_2$ (X is a labile monoanionic ligand, Y is a labile or a non-labile monoanionic ligand) as disclosed in 13 *Organometallics* 964 (1994) and in 16 *Organometallics* 3413 (1997) and EP669340A1. Diarylsilyl bridged bisindenyl dilithium reagents may also be treated with trialkyltin halides.

The diphenylsilyl bridged system may be formed between the diarylsilyldisulfonate described above and an organometallic cyclopentadienyl complex. An embodiment of the inventive synthetic process may occur in the presence of an organic solvent, or solvent mixture, a solution or slurry of an organometallic cylopentadienyl ligand with a Group 4–6 transition metal halide, preferably a titanium, zirconium, or hafnium tetrahalide, or the corresponding transition metal tetrahalide-etherate complex, for example $ZrCl_4(THF)_2$. THF is tetrahydrofuran. Removal of solvent and byproducts, such as $Me_3SnCl$ or LiCl, provides the metallocene dichloride product as a solid.

Metallocenes employing diarylsilyl bridged bisindenyl ligands are typically obtained initially as mixtures of rac and meso isomers. Isolation of rac or meso isomers may be achieved from appropriate methods such as crystallization or washing with solvent, as disclosed in WO96/19488, herein incorporated by reference for purposes of U.S. patent practice. Subsequent polymerization can be achieved with either 100% rac, 100% meso or intermediate amounts of rac and meso isomers.

The process of the present invention is suitable for the preparation of metallocenes in high purity for use in olefin polymerizations as disclosed in the copending application, filing date Feb. 8, 2001, assigned to the assignee of the present application. This is of particular importance in stereospecific polymerization of alpha olefins since only the racemic form produces stereoregular polymer. Cyclic olefin copolymers, including those of high crystalline melting point will also benefit from this method for preparing suitable metallocene catalysts where ionic catalyst system are to be use. See, for example, U.S. Pat. No. 5,324,801, herein incorporated by reference for purposes of U.S. patent practice.

The Group 4 metallocene derivatives may be activated with traditional activators, such as alumoxane activators, or with ionic activators such as described in U.S. Pat. No. 5,198,401 to form a catalyst system useful to polymerize olefins to polyolefins, e.g. polymerization of $C_{2-20}$ olefins under suitable polymerization conditions to form homopolymers or copolymers of polyethylene, polypropylene, and the like. In accordance with present invention, chiral racemic metallocene dialkyls formed are especially useful for the production of stereospecific polymer such as isotactic polypropylene. The catalyst system may be placed on a support by techniques known to those skilled in the art, such as disclosed in U.S. patent application Ser. No. 09/339,128 filed on Jun. 24, 1999, herein incorporated by reference for purposes of U.S. patent practice, or may further be used unsupported, or prepolymerized with olefinic monomer having from 2–20 carbon atoms, preferably 2 carbon atoms.

Olefin Polymerization

The diarylsilyl biscyclopentadienyl ligands described above as an embodiment of the present invention are useful for in the synthesis of metallocenes, which in turn are useful as part of a metallocene catalyst system for the polymerization of olefins to form such polymers as propylene homopolymer, copolymers of propylene, ethylene, and other alpha-olefins, and such polymers as impact copolymers. Propylene impact copolymers ("ICPs") comprise at least two major components, Component A and Component B. Component A is preferably an isotactic propylene homopolymer, though small amounts of a comonomer may be used to obtain particular properties. The end result is usually a product with lower stiffness but with some gain in impact strength compared to homopolymer Component A.

Propylene impact copolymers are commonly used in a variety of applications where strength and impact resistance are desired such as molded and extruded automobile parts, household appliances, luggage and furniture. Propylene homopolymers are often unsuitable for such applications because they are too brittle and have low impact resistance particularly at low temperature, whereas propylene impact copolymers are specifically engineered for applications such as these.

A typical propylene impact copolymer contains two phases or components, a homopolymer component and a copolymer component. These two components are usually produced in a sequential polymerization process wherein the homopolymer produced in a first reactor is transferred to a second reactor where copolymer is produced and incorporated within the matrix of the homopolymer component. The copolymer component has rubbery characteristics and provides the desired impact resistance, whereas the homopolymer component provides overall stiffness.

Many process variables influence the resulting impact copolymer and these have been extensively studied and manipulated to obtain various desired effects. For example U.S. Pat. No. 5,166,268 describes a "cold forming" process for producing propylene impact copolymers where finished articles are fabricated at temperatures below the melting point of the preform material, in this case, the propylene impact copolymer. The patented process uses a propylene impact copolymer comprised of either a homopolymer or crystalline copolymer matrix (first component) and at least ten percent by weight of an "interpolymer" of ethylene and a small amount of propylene (the second component). Adding comonomer to the first component lowers its stiffness. The ethylene/propylene copolymer second component enables the finished, cold-formed article to better maintain its shape.

More particularly, the metallocenes described above can be used to produce propylene impact copolymer compositions comprising in one embodiment:

(a) From 40% to 95% by weight Component A based on the total weight of the impact copolymer, Component A comprising propylene homopolymer or copolymer wherein the copolymer comprises 10% or less by weight ethylene, butene, hexene or octene comonomer;

(b) From 5% to 60% by weight Component B based on the total weight of the impact copolymer, Component B comprising propylene copolymer wherein the copolymer comprises from 20% to 70% by weight ethylene, butene, hexene and/or octene comonomer, and from 80% to 30% by weight propylene, wherein Component B:

(i) has a weight average molecular weight of at least 100,000;

(ii) a composition distribution of greater than 60%; and (iii) an intrinsic viscosity of greater than 1.00 dl/g.

This invention also provides a process for producing propylene impact copolymer in a multiple stage process wherein Component A comprising propylene homopolymer or copolymer wherein the copolymer comprises 10% or less by weight ethylene, butene, hexene or octene comonomer is produced in a primary stage and Component B is produced in a subsequent stage, Component B comprising propylene copolymer wherein the copolymer comprises from 20% to 70% by weight ethylene, butene, hexene and/or octene comonomer, and from 80% to 30% by weight propylene. In one embodiment, at least one of Components A and/or B are polymerized using a metallocene selected from the group consisting of: rac-diphenylsiladiyl(2-methylindenyl)$_2$zirconium dichloride; rac-diphenylsiladiyl(2-methyl-4-phenylindenyl)$_2$zirconium dichloride; and rac-diphenylsiladiyl(2-methyl-4-[1-naphthyl]indenyl)$_2$zirconium dichloride.

The propylene impact copolymers ("ICPs") of this invention comprise at least two major components, Component A and Component B. Component A is preferably an isotactic propylene homopolymer, though small amounts of a comonomer may be used to obtain particular properties. Typically such copolymers of Component A contain 10% by weight or less, preferably less than 6% by weight or less, comonomer such as ethylene, butene, hexene or octene. Most preferably less than 4% by weight ethylene is used. The end result is usually a product with lower stiffness but with some gain in impact strength compared to homopolymer Component A.

As used herein Component A refers generally to the xylene insoluble portion of the ICP composition, and Component B refers generally to the xylene soluble portion. Where the xylene soluble portion clearly has both a high molecular weight component and a low molecular weight component, we have found that the low molecular weight component is attributable to amorphous, low molecular weight propylene homopolymer. Therefore, Component B in such circumstances refers only the high molecular weight portion.

Component A preferably has a narrow molecular weight distribution Mw/Mn ("MWD"), i.e., lower than 4.0, preferably lower than 3.5, more preferably lower than 3.0, and most preferably 2.5 or lower. These molecular weight distributions are obtained in the absence of visbreaking using peroxide or other post reactor treatment designed to reduce molecular weight. Component A preferably has a weight average molecular weight (Mw as determined by GPC) of at least 100,000, preferably at least 200,000 and a melting point (Mp) of at least 145° C., preferably at least 150° C., more preferably at least 152° C., and most preferably at least 155° C.

Another important feature of ICPs is the amount of amorphous polypropylene they contain. The ICPs of this invention are characterized as having low amorphous polypropylene, preferably less than 3% by weight, more preferably less than 2% by weight, even more preferably less than 1% by weight and most preferably there is no measurable amorphous polypropylene.

Component B is most preferably a copolymer consisting essentially of propylene and ethylene although other propylene copolymers, ethylene copolymers or terpolymers may be suitable depending on the particular product properties desired. For example, propylene/butene, hexene or octene copolymers, and ethylene/butene, hexene or octene copolymers may be used, and propylene/ethylene/hexene-1 terpolymers may be used. In a preferred embodiment though, Component B is a copolymer comprising at least 40% by weight propylene, more preferably from 80% by weight to 30% by weight propylene, even more preferably from 70% by weight to 35% by weight propylene. The comonomer content of Component B is preferably in the range of from 20% to 70% by weight comonomer, more preferably from 30% to 65% by weight comonomer, even more preferably from 35% to 60% by weight comonomer. Most preferably Component B consists essentially of propylene and from 20% to 70% ethylene, more preferably from 30% to 65% ethylene, and most preferably from 35% to 60% ethylene.

For other Component B copolymers, the comonomer contents will need to be adjusted depending on the specific properties desired. For example, for ethylene/hexene copolymers, Component B should contain at least 17% by weight hexene and at least 83% by weight ethylene.

Component B, preferably has a narrow molecular weight distribution Mw/Mn ("MWD"), i.e., lower than 5.0, preferably lower than 4.0, more preferably lower than 3.5, even more preferably lower than 3.0 and most preferably 2.5 or lower. These molecular weight distributions should be obtained in the absence of visbreaking or peroxide or other post reactor treatment designed to reduce molecular weight. Component B preferably has a weight average molecular weight (Mw as determined by GPC) of at least 100,000, preferably at least 150,000, and most preferably at least 200,000.

Component B preferably has an intrinsic viscosity greater than 1.00 dl/g, more preferably greater than 1.50 dl/g and most preferably greater than 2.00 dl/g. The term "intrinsic viscosity" or "IV" is used conventionally herein to mean the viscosity of a solution of polymer such as Component B in a given solvent at a given temperature, when the polymer composition is at infinite dilution. According to the ASTM standard test method D 1601–78, IV measurement involves a standard capillary viscosity measuring device, in which the viscosity of a series of concentrations of the polymer in the solvent at the given temperature are determined. For Component B, decalin is a suitable solvent and a typical temperature is 135° C. From the values of the viscosity of solutions of varying concentrations, the "value" at infinite dilution can be determined by extrapolation.

Component B preferably has a composition distribution (CD) of greater than 60%, more preferably greater than 65%, even more preferably greater than 70%, even more preferably greater than 75%, still more preferably greater than 80%, and most preferably greater than 85%. CD defines the compositional variation among polymer chains in terms of ethylene (or other comonomer) content of the copolymer as a whole. The measurement of CD is described in detail U.S. Pat. No. 5,191,042 which is hereby fully incorporated by reference for purposes of U.S. patent practice. CD is defined herein as the weight percent of the copolymer molecules having a comonomer content within 50% of the median total molar comonomer content.

As described in U.S. Pat. No. 5,191,042, CD is established by first determining the mean ethylene (or other comonomer) content of the copolymer by a suitable test such as ASTM D-3900. Next, the copolymer sample is dissolved in solvent such as hexane and a number of fractions of differing composition are precipitated by the addition of incremental amounts of a liquid such as isopropanol in which the copolymer is insoluble. Generally from 4 to 6 fractions are precipitated in this way and the weight and ethylene (or other comonomer) content of each fraction are determined after removing the solvent. From the weight of each fraction and its ethylene content, a plot is prepared of weight percent composition vs. cumulative weight percent of polymer, and a smooth curve is drawn through the points.

Component B of the ICPs preferably has low crystallinity, preferably less than 10% by weight of a crystalline portion, more preferably less than 5% by weight of a crystalline portion. Where there is a crystalline portion of Component B, its composition is preferably the same as or at least similar to (within 15% by weight) the remainder of Component B in terms of overall comonomer weight percent.

The ICPs of this invention are "reactor produced" meaning Components A and B are not physically or mechanically blended together. Rather, they are interpolymerized in at least one reactor. The final ICP as obtained from the reactor or reactors, however, can be blended with various other components including other polymers.

The preferred melt flow rate ("MFR") of these ICPs depends on the desired end use but is typically in the range of from 0.2 dg/min to 200 dg/min, more preferably from 5 dg/min to 100 dg/min. Significantly, high MFRs, i.e., higher than 50 dg/min are obtainable.

The ICPs comprise from 40% to 95% by weight Component A and from 5% to 60% by weight Component B, preferably from 50% to 95% by weight Component A and from 5% to 50% Component B, even more preferably from 60% to 90% by weight Component A and from 10% to 40% by weight Component B. In the most preferred embodiment, the ICP consists essentially of Components A and B. The overall comonomer (preferably ethylene) content of the total ICP is preferably in the range of from 2% to 30% by weight, preferably from 5% to 25% by weight, even more preferably from 5% to 20% by weight, still more preferably from 5% to 15% by weight comonomer.

A variety of additives may be incorporated into the ICP for various purposes. Such additives include, for example, stabilizers, antioxidants, fillers, colorants, nucleating agents and mold release agents.

The ICP compositions of this invention may be prepared by conventional polymerization processes such as a two-step process. It is conceivable, although currently impractical, to commercially produce ICPs in a single reactor. Each step may be independently carried out in either the gas or liquid slurry phase. For example the first step may be conducted in the gas phase and the second in liquid slurry or vice versa. Alternatively, each phase may be the same. Preferably the ICPs of this invention are produced in multiple reactors, preferably two or three, operated in series, Component B is preferably polymerized in a second, gas phase reactor. Component A is preferably polymerized first, in a liquid slurry or solution polymerization process.

In an alternative embodiment, Component A is made in at least two reactors in order to obtain fractions with varying melt flow rate. This has been found to improve the processability of the ICP.

As used herein "stage" is defined as that portion of a polymerization process during which one component of the ICP, Component A or Component B, is produced. One or multiple reactors may be used during each stage.

Hydrogen may be added to one or both reactors to control molecular weight, IV and MFR. The use of hydrogen for such purposes is well known to those skilled in the art.

Preferably a metallocene catalyst system is used to produce the ICP compositions of this invention. To date it appears that the most suitable metallocenes are those in the generic class of bridged, substituted bis(cyclopentadienyl) metallocenes, specifically bridged, substituted bis(indenyl) metallocenes known to produce high molecular weight, high melting, highly isotactic propylene polymers. Generally speaking, those of the generic class disclosed in U.S. Pat. No. 5,770,753 (fully incorporated herein by reference) should be suitable, however, it has been found that the exact polymer obtained is highly dependent on the metallocene's specific substitution pattern.

We have found that the following racemic metallocenes are most suitable for preparing the ICP compositions of this invention: rac-diphenylsiladiyl(2-methyl-4-[phenyl]indenyl)$_2$zirconium dichloride; and rac-diphenylsiladiyl(2-methyl-4-[1-naphthyl]indenyl)$_2$zirconium dichloride. It will be immediately apparent to those skilled in the art that certain modifications to these metallocene species are not likely to result in significantly modified ICP composition though activity or ease of synthesis may be impacted. While not wishing to be bound by theory, it is believed that the critical feature of these specific metallocenes is their substitution pattern on the base indenyl group. Thus, it is believed that changing the bridge, for example substituting carbon for silicon, or changing the metal to hafnium or titanium, or changing the metal dichloride to some other dihalide or dimethyl, will not significantly change the ICP compositions of this invention. On the other hand, substituting a group at any position on the indenyl for another or adding one or more groups or substituents is likely to result in a significantly different composition which may or may not be an ICP of this invention.

Metallocenes are generally used in combination with some form of activator in order to create an active catalyst system. The term "activator" is defined herein to be any compound or component, or combination of compounds or components, capable of enhancing the ability of one or more metallocenes to polymerize olefins. Alkylalumoxanes such as methylalumoxane (MAO) are commonly used as metallocene activators. Generally alkylalumoxanes contain 5 to 40 of the repeating units:

$$R(AlRO)xAlR_2 \text{ for linear species and}$$

$$(AlRO)x \text{ for cyclic species}$$

where R is a $C_1$–$C_8$ alkyl including mixed alkyls. Compounds in which R is methyl are particularly preferred. Alumoxane solutions, particularly methylalumoxane solutions, may be obtained from commercial vendors as solutions having various concentrations. There are a variety of methods for preparing alumoxane, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,103,031 and EP-A-0 561 476, EP-B1-0 279 586, EP-A-0 594-218 and WO 94/10180, each incorporated herein by reference for purposes of U.S. patent practice.

Ionizing activators may also be used to activate metallocene dialkyls. These activators are neutral or ionic, or are compounds such as tri(n-butyl)ammonium tetrakis(pentafluorophenyl)borate, which ionize the neutral metallocene dialkyl compound. Such ionizing compounds may contain an active proton, or some other cation associated with, but not coordinated or only loosely coordinated to, the remaining ion of the ionizing compound. Combinations of activators may also be used, for example, alumoxane and ionizing activator combination, see for example, WO 94/07928, incorporated herein by reference for purposes of U.S. patent practice.

Descriptions of ionic catalysts for coordination polymerization comprised of metallocene cations activated by non-coordinating anions appear in the early work in EP-A-0 277 003, EP-A-0 277 004 and U.S. Pat. No. 5,198,401 and WO-A-92/00333 (incorporated herein by reference for purposes of U.S. patent practice). These teach desirable methods of preparation wherein metallocene (bisCp and monoCp) dialkyl or dihydrides are protonated by an anion precursor such that an alkyl/hydride group is abstracted from a transition metal to make it both cationic and charge-balanced by the non-coordinating anion. Suitable ionic salts include tetrakis-substituted borate or aluminum salts having fluorided aryl-constituents such as phenyl, biphenyl and napthyl.

The term "noncoordinating anion" (NCA) means an anion which either does not coordinate to said cation or which is only weakly coordinated to said cation thereby remaining sufficiently labile to be displaced by a neutral Lewis base. "Compatible" noncoordinating anions are those which are not degraded to neutrality when the initially formed complex decomposes. Further, the anion will not transfer an anionic substituent or fragment to the cation so as to cause it to form a neutral four coordinate metallocene compound and a neutral by-product from the anion. Particularly useful non-coordinating anions are those which are compatible, stabilize the metallocene cation in the sense of balancing its ionic charge in a +1 state, yet retain sufficient lability to permit displacement by an ethylenically or acetylenically unsaturated monomer during polymerization.

The use of ionizing ionic compounds not containing an active proton but capable of producing both the active metallocene cation and a noncoordinating anion is also known. See, for example, EP-A-0 426 637 and EP-A-0 573 403 (incorporated herein by reference for purposes of U.S. patent practice). An additional method of making the ionic catalysts uses ionizing anion precursors which are initially neutral Lewis acids but form the cation and anion upon ionizing reaction with the metallocene compounds, for example the use of tris(pentafluorophenyl) borane. See EP-A-0 520 732 (incorporated herein by reference for purposes of U.S. patent practice). Ionic catalysts for addition polymerization can also be prepared by oxidation of the metal centers of transition metal compounds by anion precursors containing metallic oxidizing groups along with the anion groups, see EP-A-0 495 375, incorporated herein by reference for purposes of U.S. patent practice.

Where the metal ligands include halogen moieties (for example, biscyclopentadienyl zirconium dichloride) which are not capable of ionizing abstraction under standard conditions, they can be converted via known alkylation reactions with organometallic compounds such as lithium or aluminum hydrides or alkyls, alkylalumoxanes, Grignard reagents, etc. See EP-A-0 500 944 and EP-A1-0 570 982 (incorporated herein by reference for purposes of U.S. patent practice) for in situ processes describing the reaction of alkyl aluminum compounds with dihalo-substituted metallocene compounds prior to or with the addition of activating anionic compounds.

Methods for supporting ionic catalysts comprising metallocene cations and NCA are described in U.S. Pat. No. 5,643,847, U.S. patent application Ser. No. 09184,358, filed Nov. 2, 1998 and U.S. patent application Ser. No. 09184389, filed Nov. 2, 1998 (all fully incorporated herein by reference for purposes of U.S. patent practice).

When the activator for the metallocene supported catalyst composition is a NCA, preferably the NCA is first added to the support composition followed by the addition of the metallocene catalyst. When the activator is MAO, preferably the MAO and metallocene catalyst are dissolved together in solution. The support is then contacted with the MAO/metallocene catalyst solution. Other methods and order of addition will be apparent to those skilled in the art.

The catalyst systems used to prepare the compositions of this invention are preferably supported using a porous particulate material, such as for example, talc, inorganic oxides, inorganic chlorides and resinous materials such as polyolefin or polymeric compounds.

Preferably, the support materials are porous inorganic oxide materials, which include those from the Periodic Table of Elements of Groups 2, 3, 4, 5, 13 or 14 metal oxides. Silica, alumina, silica-alumina, and mixtures thereof are particularly preferable. Other inorganic oxides that may be employed either alone or in combination with the silica, alumina or silica-alumina are magnesia, titania, zirconia, and the like.

Preferably the support material is porous silica which has a surface area in the range of from 10 to 700 $m^2/g$, a total pore volume in the range of from 0.1 to 4.0 cc/g and an average particle size in the range of from 10 to 500 μm. More preferably, the surface area is in the range of from 50 to 500 $m^2/g$, the pore volume is in the range of from 0.5 to 3.5 cc/g and the average particle size is in the range of from 20 to 200 μm. Most desirably the surface area is in the range of from 100 to 400 $m^2/g$, the pore volume is in the range of from 0.8 to 3.0 cc/g and the average particle size is in the range of from 30 to 100 μm. The average pore size of typical porous support materials is in the range of from 10 to 1000 Å. Preferably, a support material is used that has an average pore diameter of from 50 to 500 Å, and most desirably from 75 to 350 Å. It may be particularly desirable to dehydrate the silica at a temperature of from 100° C. to 800° C. anywhere from 3 to 24 hours.

The metallocenes, activator and support material may be combined in any number of ways. Suitable support techniques are described in U.S. Pat. Nos. 4,808,561 and 4,701,432 (each fully incorporated herein by reference for purposes of U.S. patent practice). Preferably the metallocenes and activator are combined and their reaction product supported on the porous support material as described in U.S. Pat. No. 5,240,894 and WO 94 28034, WO 96/00243, and WO 96/00245 (each fully incorporated herein by reference for purposes of U.S. patent practice). Alternatively, the metallocenes may be preactivated separately and then combined with the support material either separately or together. If the metallocenes are separately supported, then preferably, they are dried then combined as a powder before use in polymerization.

Regardless of whether the metallocenes and their activator are separately precontacted or whether the metallocenes and activator are combined at once, the total volume of reaction solution applied to porous support is desirably less than 4 times the total pore volume of the porous support, more desirably less than 3 times the total pore volume of the porous support and even more desirably in the range of from more than 1 to less than 2.5 times the total pore volume of the porous support. Procedures for measuring the total pore volume of porous support are well known in the art. One such method is described in 1 Experimental Methods in Catalyst Research 67–96 (1968).

Methods of supporting ionic catalysts comprising metallocene cations and noncoordinating anions are described in WO 91/09882, WO 94/03506, WO 96/04319 and in co-pending U.S. patent application Ser. No. 08/248,284, filed Aug. 3, 1994 (incorporated herein by reference for purposes of U.S. patent practice). The methods generally comprise either physical adsorption on traditional polymeric or inorganic supports that have been largely dehydrated and dehydroxylated, or using neutral anion precursors that are sufficiently strong Lewis acids to activate retained hydroxy groups in silica containing inorganic oxide supports such that the Lewis acid becomes covalently bound and the hydrogen of the hydroxy group is available to protonate the metallocene compounds.

The supported catalyst system may be used directly in polymerization or the catalyst system may be prepolymerized using methods well known in the art. For details regarding prepolymerization, see U.S. Pat. Nos. 4,923,833 and 4,921,825, EP 0 279 863 and EP 0 354 893 each of which is incorporated herein by reference for purposes of U.S. patent practice.

The catalyst complexes of the invention are useful in polymerization of unsaturated monomers conventionally known to be polymerizable under coordination polymerization using metallocenes. Such conditions are well known and include solution polymerization, slurry polymerization, gas-phase polymerization, and high pressure polymerization. The catalyst of the invention may be supported (preferably as described above) and as such will be particularly useful in the known operating modes employing fixed-bed, moving-bed, fluid-bed, slurry or solution processes conducted in single, series or parallel reactors. Pre-polymerization of supported catalyst of the invention may also be used for further control of polymer particle morphology in typical slurry or gas phase reaction processes in accordance with conventional teachings.

In alternative embodiments of olefin polymerization methods for this invention, the catalyst system is employed in liquid phase (solution, slurry, suspension, bulk phase or combinations thereof), in high pressure liquid or supercritical fluid phase, or in gas phase. Each of these processes may also be employed in singular, parallel or series reactors. The liquid processes comprise contacting olefin monomers with the above described catalyst system in a suitable diluent or solvent and allowing said monomers to react for a sufficient time to produce the invention copolymers. Hydrocarbyl solvents are suitable, both aliphatic and aromatic, hexane is preferred. Bulk and slurry processes are typically done by contacting the catalysts with a slurry of liquid monomer, the catalyst system being supported. Gas phase processes typically use a supported catalyst and are conducted in any manner known to be suitable for ethylene homopolymers or copolymers prepared by coordination polymerization. Illustrative examples may be found in U.S. Pat. Nos. 4,543,399, 4,588,790, 5,028,670, 5,382,638, 5,352,749, 5,408,017, 5,436,304, 5,453,471, and 5,463,999, 5,767,208 and WO 95/07942. Each is incorporated by reference for purposes of U.S. patent practice.

Generally speaking the polymerization reaction temperature can vary from 40° C. to 250° C. Preferably the polymerization reaction temperature will be from 60° C. to 220°. The pressure can vary from about 1 mm Hg to 2500 bar, preferably from 0.1 bar to 1600 bar, most preferably from 1.0 to 500 bar.

The invention is hence especially suitable for use with solution polymerization using diarylsilyl bridged systems and naphthyl containing non-coordinating anions optimized for higher temperature and/or higher molecular weight production at temperature in excess of 130 or even 170° C. and up to 250° C.

Linear polyethylene, including high and ultra-high molecular weight polyethylenes, including both homo- and copolymers with other alpha-olefin monomers, alpha-olefinic and/or non-conjugated diolefins, for example, $C_3$–$C_{20}$ olefins, diolefins or cyclic olefins, are produced by adding ethylene, and optionally one or more of the other monomers, to a reaction vessel under low pressure (typically <50 bar), at a typical temperature of 40–250° C. with the invention catalyst that has been slurried with a solvent, such as hexane or toluene. Heat of polymerization is typically removed by cooling. Gas phase polymerization can be conducted, for example, in a continuous fluid bed gas-phase reactor operated at 2000–3000 kPa and 60–160° C., using hydrogen as a reaction modifier (100–200 ppm), $C_4$–$C_8$ comonomer feedstream (0.5–1.2 mol %), and $C_2$ feedstream (25–35 mol %). See, U.S. Pat. Nos. 4,543,399, 4,588,790, 5,028,670 and 5,405,922 and 5,462,999, which are incorporated by reference for purposes of U.S. patent practice.

Ethylene-α-olefin (including ethylene-cyclic olefin and ethylene-α-olefin-diolefin) elastomers of high molecular weight and low crystallinity can be prepared utilizing the catalysts of the invention under traditional solution polymerization processes or by introducing ethylene gas into a slurry utilizing the α-olefin or cyclic olefin or mixture thereof with other monomers, polymerizable and not, as a polymerization diluent in which the invention catalyst is suspended. Typical ethylene pressures will be between 10 and 1000 psig (69–6895 kPa) and the polymerization diluent temperature will typically be between 40 and 160° C. The process can be carried out in a stirred tank reactor, or more than one operated in series or parallel. See the general disclosure of U.S. Pat. No. 5,001,205 for general process conditions. See also, international application WO 96/33227 and WO 97/22639. All documents are incorporated herein by reference for purposes of U.S. patent practice for description of polymerization processes, metallocene selection and useful scavenging compounds.

Other olefinically unsaturated monomers besides those specifically described above may be polymerized using the catalysts according to the invention, for example, styrene, alkyl-substituted styrenes, isobutylene and other geminally disubstituted olefins, ethylidene norbornene, norbornadiene, dicyclopentadiene, and other olefinically-unsaturated monomers, including other cyclic olefins, such as cyclopentene, norbornene, alkyl-substituted norbornenes, and vinyl group-containing polar monomers capable of coordination polymerization. See, for example, U.S. Pat. Nos. 5,635,573, 5,763,556, and WO 99/30822. Additionally, alpha-olefinic macromonomers of up to 1000 mer units, or more, may also be incorporated by copolymerization yielding branch-containing olefin polymers. Additionally oligomerization, dimerization, hydrogenation, olefin/carbon monoxide copolymerization, hydroformulation, hydrosilation, hydroamination and related catalytic reactions employing organometallic cationic complexes can be accomplished using the cocatalyst complexes of the invention with selected organometallic compounds as known in the art.

The catalyst compositions of the invention can be used as described above individually for coordination polymerization or can be mixed to prepare polymer blends with other known olefin polymerization catalyst compounds. By selection of monomers, blends of coordination catalyst compounds, polymer blends can be prepared under polymerization conditions analogous to those using individual catalyst compositions. Polymers having increased MWD for improved processing and other traditional benefits available from polymers made with mixed catalyst systems can thus be achieved.

The formation of blended polymers can be achieved ex situ through mechanical blending or in situ through the use of a mixed catalyst system. It is generally believed that in situ blending provides a more homogeneous product and allows the blend to be produced in one step. The use of mixed catalyst systems for in situ blending involves combining more than one catalyst in the same reactor to simultaneously produce multiple distinct polymer products. This method requires additional catalyst synthesis and the various catalyst components must be matched for their activities, the polymer products they generate at specific conditions, and their response to changes in polymerization conditions.

Where the metal ligands include hydrocarbyl moieties (for example, rac-diphenylsiladiyl(2-methylindenyl)$_2$ hafnium dimethyl) that are susceptible to ionizing abstraction, solution polymerizations of monomers can be effected by combination of such metallocenes with ionizing agents of the formula Ct+[(M)Q$_1$Q$_2$ ... Q$_i$]$^-$ and neutral Lewis acids such as tris(perfluorophenyl)borane.

Effective cations (Ct$^+$) can be any of those known to be suitable for the abstraction of any of monoanionic hydride, alkyl, or other hydrocarbyl or hydrocarbylsilyl ligands on organometallic compounds suitable as insertion polymerization catalysis, or scission of covalent metal-carbon $\eta^1$ or $\eta^2$ bonds in such organometallic compounds. Preferably the cation is essentially non-interfering with the ionic catalyst complexes formed with the organometal catalyst precursor compounds. Such include nitrogen-containing cations such as the anilinium and ammonium salts of U.S. Pat. No. 5,198,401, and WO 97/35893, the trityl carbenium cations of U.S. Pat. No. 5,387,568, metal cations, e.g., Ag$^+$, the silylium cations of WO 96/08519, and the cations of the hydrated salts of Group 1 or 2 metals of U.S. Pat. No. 5,767,208. Additionally suitable cations include nitrogen and carbon based cations described in WO 97/35893, and in copending U.S. patent application Ser. No. 60/160,942, filed 22 Oct. 1999, and Ser. No. 60/169,768, filed 9 Dec. 1999. Thus hydrocarbyl, hydrocarbyl-amine, hydrocarbyl-silyl, preferably C$_1$–C$_{20}$, and Group 1, 2, 11 and 12 metal based cations, are suitable in accordance with the invention. The teachings of these references are referred to for information and incorporated by reference for the purposes of U.S. patent practice.

The effective Group 8–15 element anionic cocatalyst complexes of the invention are, in a preferable embodiment, derived from an ionic salt, comprising a 4-coordinate Group 10–14 element anionic complex, where A$^-$ can be represented as:

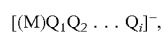

[(M)Q$_1$Q$_2$ ... Q$_i$]$^-$, where M is one or more Group 10–15 metalloid or metal, preferably boron or aluminum, and either each Q is ligand effective for providing electronic or steric effects rendering [(M')Q$_1$Q$_2$ ... Q$_n$]$^-$ suitable as a noncoordinating anion as that is understood in the art, or a sufficient number of Q are such that [(M')Q$_1$Q$_2$ ... Q$_n$]_ as a whole is an effective noncoordinating or weakly anion. Exemplary Q substituents specifically include fluorinated aryl groups, preferably perfluorinated aryl groups, and include substituted Q groups having substituents additional to the fluorine substitution, such as fluorinated hydrocarbyl groups. Preferred fluorinated aryl groups include phenyl, biphenyl, napthyl and derivatives thereof. The disclosures of U.S. Pat. Nos. 5,198, 401, 5,296,433, 5,278,119, 5,447,895, 5,688,634, 5,895,771, WO 98/02099, WO 97/29845, WO 99/43717, WO 99/42467 and copending U.S. application Ser. No. 09/261,627, filed 3 Mar. 1999, and its equivalent WO 99/45042 are particularly instructive as to suitable Q substituents and are incorporated by reference for purposes of U.S. patent practice.

Additional suitable anions are known in the art and will be suitable for use with the metallocene catalysts of the invention. See U.S. Pat. No. 5,483,014, weakly coordinating anions from borane, carborane, borate, carborate, metalloborane, or metallocarborane complexes are described and exemplified. See also, the review articles by S. H. Strauss, "The Search for Larger and More Weakly Coordinating Anions", 93 *Chem. Rev.* 927–942 (1993), and C. A. Red, "Carboranes: A New Class of Weakly Coordinating Anions for Strong Electrophiles, Oxidants and Superacids", 31 *Acc. Chem. Res.* 133–139 (1998).

The use of ionizing ionic compounds not containing an active proton but capable of producing both the active metallocene cation and a noncoordinating anion is also known. See, for example, EP-A-0 426 637 and EP-A-0 573 403 (incorporated herein by reference for purposes of U.S. patent practice). An additional method of making the ionic catalysts uses ionizing anion precursors which are initially neutral Lewis acids but form the cation and anion upon ionizing reaction with the metallocene compounds, for example the use of tris(pentafluorophenyl) borane. See EP-A-0 520 732 (incorporated herein by reference for purposes of U.S. patent practice). Ionic catalysts for addition polymerization can also be prepared by oxidation of the metal centers of transition metal compounds by anion precursors containing metallic oxidizing groups along with the anion groups, see EP-A-0 495 375 (incorporated herein by reference for purposes of U.S. patent practice).

In particular embodiments one Q group, or ligand, of the anionic complex may also be bonded to a metal/metalloid oxide support or polymeric support. See, for example, U.S. Pat. Nos. 5,427,991 and 5,939,347, each incorporated by reference for purposes of U.S. patent practice. Metal or metalloid oxide supports of the described bonding method for the invention include any metal/metalloid oxides, preferably those having surface hydroxyl groups exhibiting a pKa equal to or less than that observed for amorphous silica, i.e., pKa less than or equal to about 11. Accordingly any of the conventionally known silica support materials that retain hydroxyl groups after dehydration treatment methods will be suitable in accordance with the invention. Because of availability, both of silica and silica containing metal oxide based supports, for example, silica-alumina, are preferred. Silica particles, gels and glass beads are most typical.

Polymeric supports are preferably hydroxyl-functional-group-containing polymeric substrates, but functional groups may be any of the primary alkyl amines, secondary alkyl amines, and others, where the groups are structurally incorporated in a polymeric chain and capable of a acid-base reaction with the Lewis acid such that a ligand filling one coordination site of the Group 13 element is protonated and replaced by the polymer incorporated functionality. See, for example, the functional group containing polymers of U.S. Pat. No. 5,288,677, the functionalized polymers of U.S. Pat. No. 5,427,991 and the descriptions in copending applications U.S. patent application Ser. No. 09/277,339, filed 26 Mar. 1999, and its equivalent PCT/99US/06135, and U.S. Ser. No. 09/092,752, filed 5 Jun. 1998, and its equivalent WO 98/55518. All are incorporated by reference for purposes of U.S. patent practice.

Other known methods for supporting catalyst systems comprising a noncoordinating anion cocatalyst will also be suitable as means for supporting the catalyst complexes of this invention. Thus the catalyst complexes of the invention may also physically deposited on or affixed to a suitable support material. See, for example, the teachings of WO 91/09882, WO 93/11172, WO 96/35726 and U.S. Pat. Nos. 4,463,135, and 5,610,115.

When using the above catalysts of the invention, the total catalyst system will generally additionally comprise one or more scavenger compounds. Such compounds as used in this application and its claims is meant to include those compounds effective for removing polar impurities from the reaction environment and for increasing catalyst activity. Impurities can be inadvertently introduced with any of the polymerization reaction components, particularly with solvent, monomer and catalyst feed, and adversely affect catalyst activity and stability. It can result in decreasing or even elimination of catalytic activity, particularly when ionizing anion pre-cursors activate the catalyst system. The polar impurities, or catalyst poisons include water, oxygen, metal impurities, etc. Preferably steps are taken before provision of such into the reaction vessel, for example by chemical treatment or careful separation techniques after or during the synthesis or preparation of the various components, but some minor amounts of organometallic compound will still normally be used in the polymerization process itself.

Typically these compounds will be organometallic compounds such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, triisobutyl aluminum, methylalumoxane, and isobutyl aluminumoxane. Those compounds having bulky or $C_6$–$C_{20}$ linear hydrocarbyl substituents covalently bound to the metal or metalloid center being preferred to minimize adverse interaction with the active catalyst. Examples include triethylaluminum, but more preferably, bulky compounds such as triisobutylaluminum, triisoprenylaluminum, and long-chain linear alkyl-substituted aluminum compounds, such as tri-n-hexylaluminum, tri-n-octylaluminum, or tri-n-dodecylaluminum. When alumoxane is used as activator, any excess over the amount needed to activate the catalysts present can act as a poison scavenger compound and additional organometallic compounds may not be necessary. Alumoxanes also may be used in scavenging amounts with other means of activation, e.g., methylalumoxane and triisobutyl-aluminoxane with boron-based activators. The amount of such compounds to be used with catalyst compounds of the inventions is minimized during polymerization reactions to that amount effective to enhance activity (and with that amount necessary for activation of the catalyst compounds if used in a dual role) since excess amounts may act as catalyst poisons.

The following examples are presented to illustrate the foregoing discussion. All parts, proportions and percentages are by weight unless otherwise indicated. All examples were carried out in dry, oxygen-free environments and solvents. All solvents were purchased from commercial sources. Aluminum alkyls were purchased as hydrocarbon solutions from commercial sources. The commercial methylalumoxane ("MAO") was purchased from Albemarle as a 30 wt % solution in toluene. Although the examples may be directed to certain embodiments of the present invention, they are not to be viewed as limiting the invention in any specific respect. In these examples certain abbreviations are used to facilitate the description. These include standard chemical abbreviations for the elements and certain commonly accepted abbreviations, such as: Me=methyl, Et=ethyl, t-Bu=tertiary-butyl, Ind=indenyl, Flu=fluorenyl, THF (or thf)=tetrahydrofuran, and Ph=phenyl.

EXAMPLES

Inventive Ligand Synthesis Examples

Preparation of $Ph_2Si(indene)_2$

In the drybox, a 100 mL flask was charged with $Ph_2Si(OSO_2CF_3)_2$ (4.81 g, 10 mmol), diethyl ether (40 mL) then indenyl lithium (2.44 g, 20 mmol). After stirring overnight, the mixture was removed from the dry box and treated with water (50 mL). The aqueous layer was removed and the organic layer filtered to obtain the product as a white precipitate. Yield (from filter) 3.35 g, 8.1 mmol, 81%.

Preparation of $Ph_2Si(2\text{-methyl-4-phenylindene})_2$

In the drybox, a 100 mL flask was charged with $Ph_2Si(OSO_2CF_3)_2$ (4.81 g, 10 mmol), diethyl ether (40 mL) then 2-methyl-4-phenylindenyl lithium (4.24 g, 20 mmol). After stirring overnight, the mixture was removed from the dry box and treated with water (50 mL). The ether extracts were filtered. The product was obtained as the precipitate. Yield 3.6 g, 6.1 mmol, 61%.

Preparation of $Ph_2Si(2\text{-methyl-4-[1-napthyl]indene})_2$

In the drybox, a 250 mL flask was charged with $Ph_2Si(OSO_2CF_3)_2$ (9.6 g, 20 mmol), diethyl ether (100 mL) then 2-methyl-4-[1-napthyl]indenyl lithium (11 g, 42 mmol). After stirring for two days, half the solvent was removed and the slurry filtered through a 4–8 μm frit. The solid product was washed with additional diethyl ether (2×25 mL) then dried in vacuo. Yield 10.9 g, 15.7 mmol, 79%.

Preparation of $Ph_2Si(2\text{-methyl-4-[1-napthyl]indene})_2$ 2-methyl-4-[1-napthyl]indenyl lithium (5.5 g, 21 mmol) was added to a solution of $Ph_2Si(OSO_2CF_3)_2$ (4.8 g, 10 mmol) and diethyl ether (50 mL). The mixture was stirred overnight then the product was isolated by filtration, washed with diethyl ether (4×50 mL) then dried in vacuo. Yield 4.71 g, 6.8 mmol, 68%.

Preparation of $Ph_2Si(2\text{-methyl-4-phenylindenyl lithium})_2$ 2-methyl-4-phenylindenyl lithium was dissolved in toluene at 50° C. In a drybox, a flask was charged with $Ph_2Si(OSO_2CF_3)_2$ (9.61 g, 20 mmol), toluene (100 mL), then 2-methyl-4-phenylindenyl lithium (9.3 g, 42.6 mmol). The mixture was heated at 50° C. overnight. The mixture was filtered through celite. The celite and solids were washed with additional toluene (2×50 mL). The toluene solution of $Ph_2Si(2\text{-methyl-4-phenylindene})_2$ was treated with 2 M BuLi in pentane (20 mL, 40 mmol), stirred overnight then heated at 50° C. for 4 h then cooled to room temperature. The thick solution was poured into pentane (500 mL) causing a yellow solid to precipitate. The solid was collect by filtration, washed with pentane (4×100 mL) then dried invacuo to yield $Ph_2Si(2\text{-methyl-4-phenylindenyl lithium})_2$. Yield 10.6 g, 17.1 mmol, 85.5%.

Metallocene Synthesis via $Ph_2Si(OSO_2CF_3)_2$

Metallocene A: Preparation of $rac\text{-}Ph_2Si(2\text{-methyl-4-phenylindene})_2HfCl_2$ In the drybox, a mixture of $Ph_2Si(2\text{-methyl-4-phenylindenyl lithium})_2$ (3.07 g, 5.1 mmol) and toluene (20 mL) was treated with 1 M trimethyltin chloride (11 mL, 11 mmol). After stirring for 3 h, the mixture was filtered through celite onto a slurry of $HfCl_4$ (1.6 g, 5 mmol) and toluene (10 mL). After rinsing the celite pad with toluene (3×15 mL), the reaction was allowed to stir overnight. The mixture was dried in vacuo at 50° C. and rinsed with pentane (3×50 mL) to remove trimethyltin chloride. The remaining solids were crystallized from toluene at −30° C. to obtain $rac\text{-}Ph_2Si(2\text{-methyl-4-phenylindenyl})_2HfCl_2$. Three crops, total yield 0.95 g, 1.1 mmol, 22%.

Metallocene B: Preparation of $Ph_2Si(2\text{-methylindenyl})_2ZrCl_2$

In the drybox, a flask was charged with $Ph_2Si(2\text{-methylindenyl lithium})_2$ (2.5 g, 5.5 mmol) and ether (80 mL) then cooled to −35° C. in the freezer. The mixture was removed from the freezer then treated with $ZrCl_4$ (1.28 g, 5.5 mmol). After stirring for 2 h, the solvent was removed and the solids treated with toluene then filtered through Celite to remove LiCl. The volume of the filtrate was reduced and the solution cooled to −35° C. to achieve crystallization. Yield 0.128 g, 0.21 mmol, 3.8% of 92% $rac\text{-}Ph_2Si(2\text{-methylindenyl})_2ZrCl_2$.

Metallocene C: Preparation of $rac\text{-}Ph_2Si(2\text{-methyl-4-phenylindenyl})_2ZrCl_2$ In the drybox, a mixture of $Ph_2Si(2\text{-methyl-4-phenylindenyl lithium})_2$ (3.09 g, 5.1 mmol) and toluene (20 mL) was treated with 1 M trimethyltin chloride (11 mL, 11 mmol). After stirring for 2–3 h, the mixture was filtered through celite onto a slurry of $ZrCl_4$ (1.17 g, 5 mmol) and toluene (10 mL). After rinsing the celite pad with toluene (3×15 mL), the reaction was allowed to stir overnight then filtered through a 0.45 μm filter. The mixture was dried in vacuo at 50° C. and triturated with pentane (100 mL). The remaining solids were crystallized from toluene at −30° C. to obtain $rac\text{-}Ph_2Si(2\text{-methyl-4-phenylindenyl})_2HfCl_2$. Yield 0.4 g, 0.53 mmol, 11%.

Metallocene D: Preparation of $rac\text{-}Ph_2Si(2\text{-methyl-4-[1-napthyl]indenyl})_2ZrCl_2$ A slurry of $Ph_2Si(2\text{-methyl-4-[1-napthyl]indenyl lithium})_2$ was prepared from addition of a 2.0 M solution of n-Butyl lithium and pentane (1.5 mL, 3.0 mmol) to a mixture of $Ph_2Si(2\text{-methyl-4-[1-napthyl]indene})_2$·(1.0 g, 1.44 mmol) and diethyl ether (20 mL). After stirring for two hours, trimethyl tin chloride (0.6 g, 3.0 mmol) was added. The color changed instantly from an intense to light yellow. The ether was removed and the product extracted with pentane (3×20 mL). Removal of solvent yielded product. Yield 0.88 g, 0.86 mmol, 60%.

A 100 mL flask was charged with $ZrCl_4$ (180 mg, 0.77 mmol), toluene (20 mL) then $Ph_2Si(2\text{-methyl-4-[1-napthyl]indenyl SnMe_3})_2$ (0.815 g, 0.8 mmol). The mixture was stirred overnight then heated in vacuo at 90° C. for 48 h. The orange powder was taken up in toluene (5 mL) then filtered through a 0.45 μm filter. Diethyl ether (2–3 mL) was added to the toluene solution and the solution cooled to −30° C. After prolonged cooling crystals were isolated then washed with cold toluene (3×1 mL) then pentane (3×5 mL). After further washing with toluene (3×1 mL) and hexane (3×5 mL) the sample was dried to obtain product. Yield 17 mg, 2.6%.

Comparative Ligand Synthesis

Comparative Example: Reaction of 2-methylindenyl lithium with $Ph_2SiCl_2$

In the drybox, a scintillation vial was charged with $Ph_2SiCl_2$ (0.26 g, 1 mmol), $Et_2O$ (5 mL) then 2-methyl indenyl lithium (0.277 g, 2 mmol). The mixture was allowed to stir for 4 h, 20 min then water (5 mL) was added to quench the reaction. The mixture was removed from the box and the ether layer separated and reduced to an oil. The oil was dissolved in $CD_2Cl_2$. After drying with $MgSO_4$, the sample was examined by $^1$H NMR spectroscopy. No Ph$_2$Si(2-Methyl indene)$_2$ was observed.

Comparative Example: Reaction of 2-methyl-4-phenylindenyl lithium with Ph$_2$SiCl$_2$ In the drybox, a scintillation vial was charged with Ph$_2$SiCl$_2$ (0.26 g, 1 mmol), Et$_2$O (5 mL) then 2-methyl-4-phenylindenyl lithium (0.0.424 g, 2 mmol). The mixture was allowed to stir for 4 h, 20 min then water (5 mL) was added to quench the reaction. The mixture was removed from the box and the ether layer separated and reduced to an oil. The oil was dissolved in CD$_2$Cl$_2$. After drying with MgSO$_4$, the sample was examined by $^1$H NMR spectroscopy. No Ph$_2$Si(2-methyl-4-phenylindene)$_2$ was observed.

Supported Catalyst System

Catalyst System A. In a 100 mL round bottom flask, diphenylsiladiyl(2-methyl-4-indenyl)$_2$ hafnium dichloride (0.018 g) was added to the MAO-toluene solution (1.7 g) and stirred twenty minutes. This was filtered through a medium glass frit funnel and washed with toluene (5.3 mL). To the combined filtrates was added dehydrated silica (1.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about 2 hours and twenty minutes. The supported catalyst was recovered as an orange, free flowing solid (1.2 g). Polymerization results shown in Tables 1A and 1B.

Catalyst System B. In a 100 mL round bottom flask, diphenylsiladiyl(2-methylindenyl)$_2$ zirconium dichloride (0.050 g) was added to the MAO-toluene solution (4.8 g) and stirred twenty minutes. This was filtered through a medium glass frit funnel and washed with toluene (10 mL). To the combined filtrates was added dehydrated silica (2.85 g, Davison 948 Regular, 600° C. dehydration). This slurry was stirred for twenty minutes, then dried at 40° C. for one minute under vacuum on a rotary evaporator until the liquid evaporated and then the solid was further dried a total of about two hours and twenty eight minutes. The supported catalyst was recovered as a purple, free flowing solid (3.90 g). Polymerization results are shown in Tables 2A and 2B.

Catalyst System C. In a 100 mL round bottom flask, diphenylsiladiyl(2-methyl-4-phenylindenyl)$_2$ zirconium dichloride (0.033 g) was added to the MAO-toluene solution (3.37 g) and stirred twenty minutes. This was filtered through a medium glass frit funnel and washed with toluene (10.6 mL). To the combined filtrates was added dehydrated silica (2.85 g, Davison 948 Regular, 600° C. dehydration). This slurry was stirred for twenty minutes, then dried at 40° C. for one minute under vacuum on a rotary evaporator until the liquid evaporated and then the solid was further dried a total of about two hours and twenty eight minutes. The supported catalyst was recovered as a purple, free flowing solid (2.69 g). Polymerization results are shown in Tables 3A and 3B.

Catalyst System D. In a 100 mL round bottom flask, diphenylsiladiyl(2-methyl-4-[1-naphthyl]indenyl)$_2$ zirconium dichloride (0.017 g) was added to the MAO-toluene solution (1.52 g) and stirred twenty minutes. This was filtered through a medium glass frit funnel and washed with toluene (3.2 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about 2 hours and twenty minutes. The supported catalyst was recovered as an orange, free flowing solid (1.06 g). Polymerization results are shown in Tables 4A–4D.

Polymerizations

Polypropylene Homopolymer: The polymerization procedure for producing homopolymers with the supported catalysts was as follows. In a clean, dry two liter autoclave which had been flushed with propylene vapor, TEAL scavenger (0.3 mL, 1.5M) was added. Hydrogen gas was added at this point. The reactor was closed and filled with 800 mL liquid propylene. After heating the reactor to 70° C., the catalyst was added by washing in with propylene (200 mL). After the indicated time, typically one hour, the reactor was cooled, and the excess propylene vented. The polymer was removed and dried.

Random copolymers ("RCP"). The isotactic polypropylene homopolymer procedure was followed except that after heating to 60° C., a partial pressure of ethylene was added.

Impact Copolymers (ICP). The polymerization procedure for producing ICP with the supported catalysts was as follows. In a clean, dry two liter autoclave which had been flushed with propylene vapor, TEAL scavenger (0.3 mL, 1.5M) was added. Hydrogen gas was added at this point. The reactor was closed and filled with 800 mL liquid propylene. After heating the reactor to 70° C., the catalyst was added by washing in with propylene (200 mL). After the indicated time, typically one hour, the reactor was vented to about 170 psig pressure and then an ethylene/propylene gas mixture was passed through the reactor at the rates indicated while maintaining 200 psig. At the end of the gas phase stage, typically 90 to 150 minutes, the reactor was vented and cooled under N$_2$. The granular ICP polymer was removed and dried.

Polymer Analysis

Molecular weight determinations were made by gel permeation chromatography (GPC) according to the following technique. Molecular weights and molecular weight distributions were measured using a Waters 150° C. gel permeation chromatography equipped with Shodex (Showa Denko) AT-80 M/S columns and a differential refractive index (DRI) detector operating at 145° C. with 1,2,4-trichlorobenzene as the mobile phase at a 1.0 mL/min. flow rate. The sample injection volume was 300 microliters. The columns were calibrated using narrow polystyrene standards to generate a universal calibration curve. The polypropylene calibration curve was established using k=8.33×10$^{-5}$ and a=0.800 as the Mark-Houwink coefficients. The numerical analyses were performed using Waters "Millennium" software.

MFR is determined by a conventional procedure such as ASTM-1238 Cond. L. The ICP preferably has a melting point of at least 145° C., preferably at least 150° C., more preferably at least 152° C., and most preferably at least 155° C.

DSC melting points were determined on commercial DSC instruments and are reported as the second melting point. The polymer sample was heated to 230.0° C. for ten minutes and then cooled from 230° C. to 50° C. at 10° C./minute. The sample is held at 50° C. for five minutes. The second melt is then recorded as the sample is heated from 50° C. to 200° C. at a rate of 10° C./minute. The peak temperature is recorded as the second melting point.

Xylene Solubles. The ICP polymer was dissolved in hot xylene and then allowed to cool overnight. After filtration the insolubles are dried. The xylene soluble portion was evaporated and the soluble material recovered. The IV of the recovered soluble material was measured in decalin at 135° C. by using know methods and instruments such as a Schott A VSPro Viscosity Automatic Sampler.

FTIR analysis for the ethylene is done by standard techniques known to those skilled in the art. Calibration curves are generated from NMR techniques also known to those skilled in the art.

The improved impact strength at comparable modulus results from a higher molecular weight, as measured by IV, of Component B. The higher the molecular weight of component B, the better the impact test values.

While the present invention has been described and illustrated by reference to particular embodiments, it will be appreciated by those of ordinary skill in the art, that the invention lends itself to many different variations not illustrated herein. For these reasons, then, reference should be made solely to the appended claims for purposes of determining the true scope of the present invention. All applications to which priority is claimed and all named testing procedures are fully incorporated herein by reference.

TABLE 1A

Supported Metallocene Catalyst System A

| Run Number | Description | Catalyst Amount (mg) | Yield (g) | Efficiency (kg/g cat) | $C_2^=$ (delta psi) | Time (min) |
|---|---|---|---|---|---|---|
| 1 | RCP[1] | 405 | 22.6 | 0.06 | 20 | 22 |
| 2 | RCP | 383 | 21.6 | 0.06 | 20 | 60 |

[1]RCP = random copolymers

TABLE 1B

Supported Metallocene Catalyst System A

| Run Number | Total ethylene (wt %) | Melting Point of Polymer (° C.) | MW (×10$^{-3}$) | MWD |
|---|---|---|---|---|
| 1 | 1.37 | 144.2 | 416.633 | 2.67 |
|   |      | 139.1 | 337.0   | 2.98 |
| 2 | 3.04 | 142.8 | 513.0   | 2.65 |

TABLE 2A

Supported Metallocene Catalyst System B

| Run Number | Description | Catalyst Amount (mg) | Yield (g) | Efficiency (kg/g cat) | $C_2^=$ partial pressure (psi) | $H_2$ (mmole) | Time (min) |
|---|---|---|---|---|---|---|---|
| 3 | HomoPP[1] | 124 | 20.3 | 0.16 | 0 | 0 | 60 |
| 4 | HomoPP    | 120 | 26.4 | 0.22 | 5 | 0 | 60 |

[1]homoPP = homopolymer of propylene.

TABLE 2B

Supported Metallocene Catalyst System B

| Run Number | Total ethylene (wt %) | Final MFR (dg/min) | Melting Point (° C.) | MW (×10$^{-3}$) | MWD |
|---|---|---|---|---|---|
| 3 | — | 1.29 | 142.3 | 355.5 | 2.07 |
| 4 | 1.8 | 4.48 | 129.7 | 257.9 | 2.03 |

TABLE 3A

Supported Metallocene Catalyst System C

| Run Number | Description | Catalyst Amount (mg) | Yield (g) | Efficiency (kg/g cat) | $C_2^=$ (delta psi) | $H_2$ (mmole) | Time Split[1] (min) | $C_2^=/C_3^=$ flow rates (l/min.) |
|---|---|---|---|---|---|---|---|---|
| 5 | RCP | 40 | 186.7 | 4.67 | 20 | 0 | 60 | — |
| 6 | RCP | 42 | 50.9 | 1.21 | 0 | 0 | 60 | — |
| 7 | RCP | 44 | 264.1 | 6.00 | 55 | 0 | 60 | — |
| 8 | RCP | 40 | 112.5 | 2.81 | 10 | 0 | 60 | — |
| 9 | HomoPP | 61 | 190.2 | 3.12 | — | 77.5 | 30 | — |
| 10 | ICP | 31 | 205.6 | 6.63 | — | 77.5 | 60/90 | 4.0/1.0 |
| 11 | ICP | 33 | 218.1 | 6.61 | — | 77.5 | 60/150 | 4.0/1.0 |
| 12 | ICP | 31 | 243.9 | 7.87 | — | 77.5 | 60/150 | 4.1/0.9 |
| 13 | ICP | 30 | 223.3 | 7.44 | — | 77.5 | 60/150 | 3.6/1.4 |
| 14 | HomoPP | 30 | 155.1 | 5.17 | — | 77.5 | 60 | — |

[1]The time split refers to the two times of reaction: one time for the homopolypropylene reaction and another time for the copolymer reaction.

TABLE 3B

Supported Metallocene System C

| Run Number | Total Ethylene (wt %) | Ethylene in Component B (wt %) | Total Component B (wt %) | Final MFR (dg/min) | Melting Point (° C.) | MW ($\times 10^{-3}$) | MWD | IV of Component B |
|---|---|---|---|---|---|---|---|---|
| 5 | 1.14 | — | — | 0.66 | 140.83 | 425.3 | 2.48 | — |
| 6 | — | — | — | 0.01 | 148.6 | 879.9 | 2.78 | — |
| 7 | 3.17 | — | — | 2.23 | 125.4 | 313.8 | 2.11 | — |
| 8 | 0.55 | — | — | 0.21 | 144.6 | 542.0 | 2.32 | — |
| 9 | — | — | — | 351.9 | 150.0 | 77.4 | 2.90 | — |
| 10 | 4.97 | 49.84 | 9.97 | 378.3 | 151.1 | 83.3 | 2.47 | 0.9957 |
| 11 | 9.10 | 48.23 | 18.87 | 259.6 | 150.2 | 86.3 | 2.39 | 0.9989 |
| 12 | 10.24 | 50.80 | 20.16 | 114.0 | 151.1 | 103.5 | 2.88 | 0.9786 |
| 13 | 7.12 | 38.25 | 18.61 | 213.17 | 150.2 | 90.5 | 2.49 | 0.9142 |
| 14 | — | — | — | 459.2 | 150.2 | 75.4 | 3.15 | — |

TABLE 4A

Supported Metallocene Catalyst System D.

| Run Number | Catalyst Amount (mg) | Yield (g) | Efficiency (kg/g cat) | $H_2$ (mmole) | Time split (min) | $C_2^=/C_3^=$ flow rates (l/min.) |
|---|---|---|---|---|---|---|
| 15 | 31 | 243.9 | 7.87 | 78 | 60/150 | 4.1/0.9 |
| 16 | 30 | 155.1 | 5.17 | 78 | 60 | — |
| 17 | 43 | 139.0 | 3.23 | 62 | 60 | — |
| 18 | 44 | 154.0 | 3.50 | 62 | 60/150 | 4.1/0.9 |
| 19 | 43 | 102.2 | 2.38 | 62 | 60/150 | 2.6/1.4 |
| 20 | 43 | 81.1 | 1.89 | 78 | 60/150 | 4.0/1.0 |
| 21 | 41 | 53.3 | 1.30 | 78 | 60 | — |

TABLE 4B

Supported Metallocene Catalyst System D

| Run Number | Total Ethylene (wt %) | Ethylene in Component B (wt %) | Total Component B (wt %) | Final MFR (dg/min) | Melting Point (° C.) | MW ($\times 10^{-3}$) | MWD | Comp. B IV |
|---|---|---|---|---|---|---|---|---|
| 15 | 10.24 | 50.80 | 20.16 | 114.0 | 151.1 | 103.5 | 2.88 | 0.9786 |
| 16 | — | — | — | 459.2 | 150.2 | 75.4 | 3.15 | — |
| 17 | — | — | — | 10.3 | 151.83, minor 138.33 | 225.6 | 1.93 | — |
| 18 | 10.95 | 50.37 | 21.74 | 3.66 | 151.97 | 302.3 | 2.78 | 2.185 |
| 19 | 6.46 | 36.4 | 17.75 | 7.01 | 152.77 | 240.3 | 2.44 | 2.11 |

TABLE 4B-continued

Supported Metallocene Catalyst System D

| Run Number | Total Ethylene (wt %) | Ethylene in Component B (wt %) | Total Component B (wt %) | Final MFR (dg/min) | Melting Point (° C.) | MW (×10$^{-3}$) | MWD | Comp. B IV |
|---|---|---|---|---|---|---|---|---|
| 20 | 9.37 | 47.34 | 19.79 | 131.01 | 150.83 | 122.6 | 4.26 | 2.063 |
| 21 | — | — | — | 681.8 | 151.23 | 76.9 | 3.5 | — |

TABLE 4C

Supported Metallocene System D

| Run Number | Description | MFR (dg/min) | % Xylene Solubles (wt %) | % Xylene Insolubles (wt %) | FTIR DATA Total C$_2$ | C$_2$ in Comp. B | Total Comp. B | IV of Comp. B |
|---|---|---|---|---|---|---|---|---|
| 15 | ICP | 114.0 | 25.6 | 74.5 | 10.24 | 50.8 | 20.2 | 0.979 |
| 16 | HomoPP | 459.2 | 1.2 | 98.8 | — | — | — | — |
| 17 | HomoPP | 10.3 | 0.7 | 99.3 | — | — | — | — |
| 18 | ICP | 3.66 | 24 | 75.6 | 10.95 | 50.37 | 21.7 | 2.185 |
| 19 | ICP | 7.01 | 20.9 | 79.3 | 6.46 | 36.4 | 17.7 | 2.11 |
| 20 | ICP | 131.01 | 22 | 78.1 | 9.37 | 47.34 | 19.8 | 2.06 |
| 21 | homoPP | 681.9 | 2.1 | 98 | — | — | — | — |

TABLE 4D

Supported Metallocene Catalyst System D

| Run No. | Descr. | MFR (dg/min) | Xylene Solubles (low MW peak)[1] | | | | Xylene Solubles (high MW peak)[2] | | | | Xylene Insolubles | | | |
|---|---|---|---|---|---|---|---|---|---|---|---|---|---|---|
| | | | Mn | Mw | Mz | Mw/Mn | Mn | Mw | Mz | Mw/Mn | Mn | Mw | Mz | Mw/Mn |
| 15 | ICP | 114.0 | 1251 | 1554 | 1874 | 1.24 | 38015 | 74567 | 115589 | 1.96 | 12314 | 32426 | 54966 | 2.63 |
| 16 | HomoPP | 459.2 | 1513 | 2013 | 2599 | 1.33 | 18384 | 30191 | 45639 | 1.64 | 17552 | 41149 | 67038 | 2.34 |
| 17 | HomoPP | 10.3 | 1114 | 1383 | 1715 | 1.24 | 12228 | 23656 | 42278 | 1.93 | 82347 | 184675 | 309914 | 2.24 |
| 18 | ICP | 3.66 | 929 | 1153 | 1502 | 1.24 | 77378 | 211252 | 413832 | 2.73 | 97431 | 248553 | 471070 | 2.55 |
| 19 | ICP | 7.01 | 982 | 1165 | 1403 | 1.19 | 57316 | 166144 | 312133 | 2.9 | 85158 | 206876 | 354334 | 2.43 |
| 20 | ICP | 131.01 | 1515 | 2556 | 4282 | 1.69 | 74803 | 161031 | 319874 | 2.15 | 27750 | 76477 | 129002 | 2.70 |
| 21 | homoPP | 681.8 | 1430 | 1868 | 2472 | 1.31 | 10530 | 13500 | 17834 | 1.28 | 24398 | 76119 | 137103 | 3.12 |

[1]The "low" peak refers to the peak resulting from the detector in the GPC.
[2]The "high" peak refers to the peak resulting from the detector in the GPC.

What is claimed is:

1. A method of forming a diaryl bridged biscyclopentadienyl metallocene component, the method comprising combining in a suitable solvent a diarylmetaldisulfonate moiety with a organometallic cyclopentadienyl moiety to form a diarylmetal bridged biscyclopentadienyl compound; and
   combining the diarylmetal bridged biscyclopentadienyl compound with a Group 4 metal.

2. The method of claim 1, wherein the diarylmetaldisulfonate is described as follows:

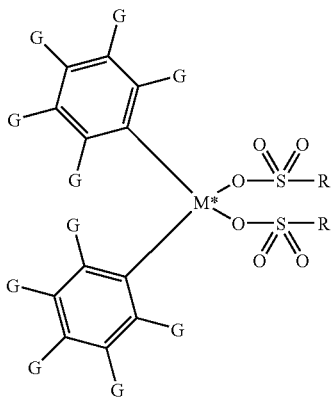

wherein G is the same or different and are a hydrogen, alkyl, haloalkyl, vinyl, aryl, alkynyl, silyl, germyl, amine, ammonium, phosphine, phosphonium, ether, thioether, fluoro, dilate, bromo, iodo, borane, borate, alane or aluminate groups or any combination of such groups; and wherein adjacent G groups from each aryl group may join to form a ring system of 2 to 8 carbon atoms and also contain an amine, silyl, or ether group; and wherein the aryl groups may be joined at the corresponding ortho (2) positions by a covalent bond;
   and wherein the aryl groups may also be heterocycles that are aromatic;
   and wherein the aryl rings may also be substituted by annulated rings such annulated aryl rings are napthyl, tetrahydronapthyl, phenanthryl and fluorenyl;
   and wherein the aryl rings may also be substituted by additional silylsulfonates;
   and wherein the two aryl groups bound to the silyldisulfonate fragment may also be joined together directly, as in a substituted biphenyl derivative or by linker groups; wherein the linker group is an alkyl, vinyl, phenyl, alkynyl, silyl, germyl, amine, ammonium, phosphine, phosphonium, ether, thioether, borane, borate, alane or aluminate groups;
   wherein M* is Si, Sn or Ge; and
   wherein the R groups may be the same or different, and are an alkyl, perhaloalkyl, phenyl, perhalophenyl, 3. The method of claim 1, wherein the organometallic cyclopentadienyl moiety is described as follows:

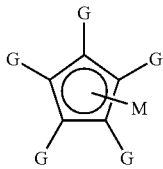

wherein G is the same or different and are a hydrogen, alkyl, haloalkyl, vinyl, aryl, alkynyl, silyl, germyl, amine, ammonium, phosphine, phosphonium, ether, thioether, fluoro, chloro, bromo, iodo, borane, borate, alane or aluminate groups or any combination of such groups; and wherein adjacent G groups from each aryl group may join to form a ring system of 2 to 8 carbon atoms and also contain an amine, silyl, or ether group; and wherein M is a metal such as Li, Na, or K.

4. The method of claim 3, wherein the organometallic cyclopentadienyl moiety is an indenyl moiety.

5. The method of claim 2, wherein the diarylmetaldisulfonate moiety is selected from the group consisting of:
diphenylsilylditriflate
di-2-naphthylsilylditriflate
(2-methyl-4-phenyl-5-methyl)(4-trimethylsiloxy)silylditriflate
di(2,4,6-trimethylphenyl)silylditriflate
di-5-tetrahydronaphthylsilylditriflate
di(4-triethylsilylphenyl)silylditriflate
di(3,5-ditrifluoromethylphenyl)silylditriflate
(4-dimethysilyltriflate)(phenyl)silylditriflate
di(diphenylsilylditriflate)
bis(4-methylphenyl)(2,5-di-tert-butylpyridine)silylditriflate
di(biphenyl)silylditriflate
di(2-ethylphenyl)silylditriflate
4,5-(9,10-dihydrophenanthryl)silylditriflate
biphenylsilylditriflate
phenanthra-4,5-silylditriflate
naptha-4,5-silylditriflate.

6. The method of claim 4, wherein the organometallic cyclopentadienyl moiety is selected from the group consisting of indenyl lithium, 2-methylindenyl lithium, 2-ethylindenyl lithium, 2-isopropylindenyl lithium, 4,6-dimethylindenyl lithium, 2,4,6-trimethylindenyl lithium, 2-ethyl,-4,6-dimethylindenyl lithium, 2-isopropyl-4,6-dimethylindenyl lithium, 4,6-diisopropylindenyl lithium, 2-methyl-4,6-diisopropylindenyl lithium, 2-ethyl-4,6-diisopropylindenyl lithium, 4,5-benzoindenyl lithium, 4,5-benzo-2-methylindenyl lithium, 4,5-benzo-2-ethylindenyl lithium, 4,5-benzo-2-isopropylindenyl lithium, 4,5-cyclohexylindenyl lithium, 4,5-cyclohexyl-2-methylindenyl lithium, 4,5-cyclohexyl-2-ethylindenyl lithium, 4,5-cyclclohexyl-2-isopropylindenyl lithium, 4-phenylindenyl lithium, 2-methyl-4-phenylindenyl lithium, 2-ethyl-4-phenylindenyl lithium, 2-propyl-4-phenylindenyl lithium, 4-phenyl-6-methylindenyl lithium, 2,6-dimethyl-4-phenylindenyl lithium, 2-ethyl-4-phenyl-6-methylindenyl lithium, 2-isopropyl-4-phenyl-6-methylindenyl lithium, 4-[1-naphthyl]indenyl lithium, 2-methyl-4-[1-naphthyl]indenyl lithium, 2-ethyl-4-[1-naphthyl]indenyl lithium, 2-isopropyl-4-[1-naphthyl]indenyl lithium, 4-[1-naphthyl]-6-methylindenyl lithium, 2,6-dimethyl-4-[1-naphthyl]indenyl lithium, 2-ethyl-4-[1-naphthyl]-6-methylindenyl lithium, 2-isopropyl-4-[1-naphthyl]-6-methylindenyl lithium, 4-(3,5-dimethylphenyl)indenyl lithium, 2-methyl-4-(3,5-dimethylphenyl)indenyl lithium, 2-ethyl-4-(3,5-dimethylphenyl)indenyl lithium, 2-isopropyl-4-(3,5-dimethylphenyl)indenyl lithium, 6-methyl-4-(3,5-dimethylphenyl)indenyl lithium, 2,6-dimethyl-4-(3,5-dimethylphenyl)indenyl lithium, 2-ethyl-4-(3,5-dimethylphenyl)-4-methylindenyl lithium, 2-isopropyl-4-(3,5-dimethylphenyl)6-methylindenyl lithium, 4-(3,5-di-tert-butylphenyl)indenyl lithium, 2-methyl-4-(3 ,5-di-tert-butylphenyl)indenyl lithium, 2-ethyl-4-(3,5-di-tert-butylphenyl)indenyl lithium, 2-isopropyl-4-(3,5-di-tert-butylphenyl)indenyl lithium, 6-methyl-4-(3,5-di-tert-butylphenyl)indenyl lithium, 2,6-dimethyl-4-(3,5-di-tert-butylphenyl)indenyl lithium, 2-ethyl-4-(3,5-di-tert-butylphenyl)-6-methylindenyl lithium, and 2-isopropyl-4-(3,5-di-tert-butylphenyl)6-methylindenyl lithium.

7. The method of claim 2, wherein the diarylmetaldisulfonate moiety is $Ph_2Si(OSO_2CF_3)_2$.

* * * * *